(12) United States Patent
Olson et al.

(10) Patent No.: US 8,939,344 B2
(45) Date of Patent: *Jan. 27, 2015

(54) SURGICAL STAPLING APPARATUS

(71) Applicant: Covidien LP, Mansfield, MA (US)

(72) Inventors: Lee Ann Olson, Wallingford, CT (US);
Ernest Aranyi, Easton, CT (US);
Patrick Mozdzierz, Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/161,027

(22) Filed: Jan. 22, 2014

(65) Prior Publication Data

US 2014/0130330 A1 May 15, 2014

Related U.S. Application Data

(63) Continuation of application No. 13/787,921, filed on Mar. 7, 2013, now Pat. No. 8,757,466, which is a continuation of application No. 13/223,519, filed on Sep. 1, 2011, now Pat. No. 8,408,440, which is a continuation of application No. 12/414,931, filed on Mar. 31, 2009, now Pat. No. 8,016,178.

(51) Int. Cl.
*A61B 17/04* (2006.01)
*A61B 17/10* (2006.01)
(Continued)

(52) U.S. Cl.
CPC ......... *A61B 17/068* (2013.01); *A61B 17/07207* (2013.01); *A61B 17/07292* (2013.01); *A61B 2017/07214* (2013.01); *A61B 2017/07271* (2013.01)
USPC ..................................................... 227/176.1

(58) Field of Classification Search
CPC .............. A61B 17/07292; A61B 17/00; A61B 17/0057; A61B 17/0469; A61B 17/0483; A61B 17/0401; A61B 17/0487; A61B 2017/0409; A61F 2210/00
USPC ............ 227/175.1–182.1; 606/139, 151, 154, 606/215, 216, 219

See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov |

(Continued)

FOREIGN PATENT DOCUMENTS

| | | |
|---|---|---|
| CA | 2 667 434 | 5/2008 |
| DE | 1 99 24 311 | 11/2000 |

(Continued)

OTHER PUBLICATIONS

European Search Report corresponding to EP 05 02 2585.3, completed Jan. 25, 2006 and mailed Feb. 3, 2006; (4 pp).

(Continued)

*Primary Examiner* — Robert Long

(57) ABSTRACT

A loading unit for use with a surgical stapling apparatus is provided and includes a tool assembly having a cartridge assembly and an anvil assembly that are movable in relation to one another; a surgical buttress releasably secured to a tissue contacting surface of the anvil assembly and/or the cartridge assembly, wherein each surgical buttress is secured to the anvil assembly and/or the cartridge assembly by at least one anchor; a release assembly associated with the anvil assembly and/or the cartridge assembly; and a drive assembly slidably translatable through the tool assembly between proximal and distal positions, wherein the drive assembly actuates the release assembly to thereby release the anchor to free the surgical buttress from the anvil assembly and/or the cartridge assembly.

20 Claims, 24 Drawing Sheets

(51) Int. Cl.
*A61B 17/068* (2006.01)
*A61B 17/072* (2006.01)

(56) References Cited

U.S. PATENT DOCUMENTS

| | | | |
|---|---|---|---|
| 3,124,136 A | 3/1964 | Usher |
| 3,490,675 A | 1/1970 | Green |
| 3,499,591 A | 3/1970 | Green |
| 4,347,847 A | 9/1982 | Usher |
| 4,354,628 A | 10/1982 | Green |
| 4,429,695 A | 2/1984 | Green |
| 4,452,245 A | 6/1984 | Usher |
| 4,605,730 A | 8/1986 | Shalaby |
| 4,655,221 A | 4/1987 | Devereux |
| 4,834,090 A | 5/1989 | Moore |
| 4,838,884 A | 6/1989 | Dumican |
| 4,927,640 A | 5/1990 | Dahlinder |
| 4,930,674 A | 6/1990 | Barak |
| 5,002,551 A | 3/1991 | Linsky |
| 5,014,899 A | 5/1991 | Presty |
| 5,040,715 A | 8/1991 | Green |
| 5,065,929 A | 11/1991 | Schulze |
| 5,205,459 A | 4/1993 | Brinkerhoff |
| 5,263,629 A | 11/1993 | Trumbull |
| 5,307,976 A | 5/1994 | Olson |
| 5,312,023 A | 5/1994 | Green |
| 5,314,471 A | 5/1994 | Brauker |
| 5,318,221 A | 6/1994 | Green |
| 5,326,013 A | 7/1994 | Green |
| 5,332,142 A | 7/1994 | Robinson |
| 5,344,454 A | 9/1994 | Clarke |
| 5,392,979 A | 2/1995 | Green |
| 5,397,324 A | 3/1995 | Carroll |
| 5,425,745 A | 6/1995 | Green |
| 5,441,193 A | 8/1995 | Gravener |
| 5,441,507 A | 8/1995 | Wilk |
| 5,443,198 A | 8/1995 | Viola |
| 5,468,253 A | 11/1995 | Bezwada |
| 5,503,638 A | 4/1996 | Cooper |
| 5,542,594 A | 8/1996 | McKean |
| 5,549,628 A | 8/1996 | Cooper |
| 5,575,803 A | 11/1996 | Cooper |
| 5,653,756 A | 8/1997 | Clarke |
| 5,683,809 A | 11/1997 | Freeman |
| 5,690,675 A | 11/1997 | Sawyer |
| 5,702,409 A | 12/1997 | Rayburn |
| 5,752,965 A | 5/1998 | Francis |
| 5,762,256 A | 6/1998 | Mastri |
| 5,766,188 A | 6/1998 | Igaki |
| 5,769,892 A | 6/1998 | Kingwell |
| 5,782,396 A | 7/1998 | Mastri |
| 5,799,857 A | 9/1998 | Robertson |
| 5,810,855 A | 9/1998 | Rayburn |
| 5,814,057 A | 9/1998 | Oi |
| 5,833,695 A | 11/1998 | Yoon |
| 5,843,096 A | 12/1998 | Igaki |
| 5,895,412 A | 4/1999 | Tucker |
| 5,895,415 A | 4/1999 | Chow |
| 5,902,312 A | 5/1999 | Frater |
| 5,908,427 A | 6/1999 | McKean |
| 5,915,616 A | 6/1999 | Viola |
| 5,931,847 A | 8/1999 | Bittner |
| 5,964,774 A | 10/1999 | McKean |
| 5,997,895 A | 12/1999 | Narotam |
| 6,019,791 A | 2/2000 | Wood |
| 6,030,392 A | 2/2000 | Dakov |
| 6,032,849 A | 3/2000 | Mastri |
| 6,045,560 A | 4/2000 | McKean |
| 6,063,097 A | 5/2000 | Oi |
| 6,080,169 A | 6/2000 | Turtel |
| 6,099,551 A | 8/2000 | Gabbay |
| 6,149,667 A | 11/2000 | Hovland |
| 6,155,265 A | 12/2000 | Hammerslag |
| 6,210,439 B1 | 4/2001 | Firmin |
| 6,214,020 B1 | 4/2001 | Mulhauser |
| 6,241,139 B1 | 6/2001 | Milliman |
| 6,258,107 B1 | 7/2001 | Balazs |
| 6,267,772 B1 | 7/2001 | Mulhauser |
| 6,273,897 B1 | 8/2001 | Dalessandro |
| 6,280,453 B1 | 8/2001 | Kugel |
| 6,299,631 B1 | 10/2001 | Shalaby |
| 6,312,457 B1 | 11/2001 | DiMatteo |
| 6,312,474 B1 | 11/2001 | Francis |
| 6,325,810 B1 | 12/2001 | Hamilton |
| 6,436,030 B2 | 8/2002 | Rehil |
| 6,454,780 B1 | 9/2002 | Wallace |
| 6,461,368 B2 | 10/2002 | Fogarty |
| 6,503,257 B2 | 1/2003 | Grant |
| 6,514,283 B2 | 2/2003 | DiMatteo |
| 6,517,566 B1 | 2/2003 | Hovland |
| 6,551,356 B2 | 4/2003 | Rousseau |
| 6,592,597 B2 | 7/2003 | Grant |
| 6,638,285 B2 | 10/2003 | Gabbay |
| 6,652,594 B2 | 11/2003 | Francis |
| 6,656,193 B2 | 12/2003 | Grant |
| 6,669,735 B1 | 12/2003 | Pelissier |
| 6,677,258 B2 | 1/2004 | Carroll |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois |
| 6,736,854 B2 | 5/2004 | Vadurro |
| 6,746,458 B1 | 6/2004 | Cloud |
| 6,773,458 B1 | 8/2004 | Brauker |
| 6,896,684 B2 | 5/2005 | Monassevitch |
| 6,927,315 B1 | 8/2005 | Heinecke |
| 6,939,358 B2 | 9/2005 | Palacios |
| 6,946,196 B2 | 9/2005 | Foss |
| 6,959,851 B2 | 11/2005 | Heinrich |
| 7,055,730 B2 | 6/2006 | Ehrenfels |
| 7,060,087 B2 | 6/2006 | DiMatteo |
| 7,087,065 B2 | 8/2006 | Ulmsten |
| 7,108,701 B2 | 9/2006 | Evens |
| 7,128,253 B2 | 10/2006 | Mastri |
| 7,128,748 B2 | 10/2006 | Mooradian |
| 7,141,055 B2 | 11/2006 | Abrams |
| 7,147,138 B2 | 12/2006 | Shelton, IV |
| 7,160,299 B2 | 1/2007 | Baily |
| 7,232,449 B2 | 6/2007 | Sharkawy |
| 7,241,300 B2 | 7/2007 | Sharkawy |
| 7,293,685 B2 | 11/2007 | Ehrenfels |
| 7,307,031 B2 | 12/2007 | Carroll |
| 7,311,720 B2 | 12/2007 | Mueller |
| 7,377,928 B2 | 5/2008 | Zubik |
| 7,434,717 B2 | 10/2008 | Shelton, IV |
| 7,438,209 B1 | 10/2008 | Hess |
| 7,547,312 B2 | 6/2009 | Bauman |
| 7,559,937 B2 | 7/2009 | de la Torre |
| 7,594,921 B2 | 9/2009 | Browning |
| 7,604,151 B2 | 10/2009 | Hess |
| 7,665,646 B2 | 2/2010 | Prommersberger |
| 7,666,198 B2 | 2/2010 | Suyker |
| 7,669,747 B2 | 3/2010 | Weisenburgh, II |
| 7,717,313 B2 | 5/2010 | Bettuchi |
| 7,722,642 B2 | 5/2010 | Williamson, IV |
| 7,744,627 B2 | 6/2010 | Orban, III |
| 7,776,060 B2 | 8/2010 | Mooradian |
| 7,793,813 B2 | 9/2010 | Bettuchi |
| 7,799,026 B2 | 9/2010 | Schechter |
| 7,823,592 B2 | 11/2010 | Bettuchi |
| 7,824,420 B2 | 11/2010 | Eldridge |
| 7,845,533 B2 | 12/2010 | Marczyk |
| 7,845,536 B2 | 12/2010 | Viola |
| 7,846,149 B2 | 12/2010 | Jankowski |
| 7,857,185 B2 | 12/2010 | Swayze |
| 7,892,247 B2 | 2/2011 | Conston |
| 7,909,224 B2 | 3/2011 | Prommersberger |
| 7,909,837 B2 | 3/2011 | Crows |
| 7,938,307 B2 | 5/2011 | Bettuchi |
| 7,942,890 B2 | 5/2011 | D'Agostino |
| 7,950,561 B2 | 5/2011 | Aranyi |
| 7,951,166 B2 | 5/2011 | Orban |

(56) References Cited

U.S. PATENT DOCUMENTS

| | | |
|---|---|---|
| 7,967,179 B2 | 6/2011 | Olson |
| 7,988,027 B2 | 8/2011 | Olson |
| 8,011,550 B2 | 9/2011 | Aranyi |
| 8,011,555 B2 | 9/2011 | Tarinelli |
| 8,016,177 B2 | 9/2011 | Bettuchi |
| 8,016,178 B2 | 9/2011 | Olson |
| 8,028,883 B2 | 10/2011 | Stopek |
| 8,038,045 B2 | 10/2011 | Bettuchi |
| 8,062,330 B2 | 11/2011 | Prommersberger |
| 8,083,119 B2 | 12/2011 | Prommersberger |
| 8,123,766 B2 | 2/2012 | Bauman |
| 8,123,767 B2 | 2/2012 | Bauman |
| 8,146,791 B2 | 4/2012 | Bettuchi |
| 8,157,149 B2 | 4/2012 | Olson |
| 8,157,151 B2 | 4/2012 | Ingmanson |
| 8,167,895 B2 | 5/2012 | D'Agostino |
| 8,192,460 B2 | 6/2012 | Orban |
| 8,210,414 B2 | 7/2012 | Bettuchi |
| 8,225,799 B2 | 7/2012 | Bettuchi |
| 8,225,981 B2 | 7/2012 | Criscuolo |
| 8,231,043 B2 | 7/2012 | Tarinelli |
| 8,235,273 B2 | 8/2012 | Olson |
| 8,245,901 B2 | 8/2012 | Stopek |
| 8,256,654 B2 | 9/2012 | Bettuchi |
| 8,257,391 B2 | 9/2012 | Orban |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi |
| 8,308,046 B2 | 11/2012 | Prommersberger |
| 8,312,885 B2 | 11/2012 | Bettuchi |
| 8,313,014 B2 | 11/2012 | Bettuchi |
| 8,348,126 B2 | 1/2013 | Olson |
| 8,348,130 B2 * | 1/2013 | Shah et al. ............... 227/180.1 |
| 8,365,972 B2 | 2/2013 | Aranyi |
| 8,371,491 B2 | 2/2013 | Huitema |
| 8,371,492 B2 * | 2/2013 | Aranyi et al. ............ 227/176.1 |
| 8,371,493 B2 * | 2/2013 | Aranyi et al. ............ 227/176.1 |
| 8,393,514 B2 | 3/2013 | Shelton, IV |
| 8,408,440 B2 * | 4/2013 | Olson et al. ............. 227/178.1 |
| 8,413,871 B2 | 4/2013 | Racenet |
| 8,424,742 B2 | 4/2013 | Bettuchi |
| 8,453,652 B2 | 6/2013 | Stopek |
| 8,453,904 B2 | 6/2013 | Eskaros |
| 8,453,909 B2 | 6/2013 | Olson |
| 8,453,910 B2 | 6/2013 | Bettuchi |
| 8,464,925 B2 | 6/2013 | Hull |
| 8,474,677 B2 | 7/2013 | Woodard, Jr. |
| 8,479,968 B2 | 7/2013 | Hodgkinson |
| 8,485,414 B2 | 7/2013 | Criscuolo |
| 8,496,683 B2 * | 7/2013 | Prommersberger et al. .. 606/215 |
| 8,511,533 B2 | 8/2013 | Viola |
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Prommersberger |
| 8,631,989 B2 | 1/2014 | Aranyi |
| 8,668,129 B2 | 3/2014 | Olson |
| 8,672,206 B2 * | 3/2014 | Aranyi et al. ............ 227/176.1 |
| 8,684,250 B2 | 4/2014 | Bettuchi |
| 8,757,466 B2 | 6/2014 | Olson |
| 8,789,737 B2 | 7/2014 | Hodgkinson |
| 8,820,606 B2 | 9/2014 | Hodgkinson |
| 2002/0028243 A1 | 3/2002 | Masters |
| 2002/0091397 A1 | 7/2002 | Chen |
| 2003/0065345 A1 | 4/2003 | Weadock |
| 2003/0083676 A1 | 5/2003 | Wallace |
| 2003/0120284 A1 | 6/2003 | Palacios |
| 2003/0181927 A1 | 9/2003 | Wallace |
| 2003/0183671 A1 | 10/2003 | Mooradian |
| 2003/0208231 A1 | 11/2003 | Williamson, IV |
| 2004/0107006 A1 | 6/2004 | Francis |
| 2004/0254590 A1 | 12/2004 | Hoffman |
| 2004/0260315 A1 | 12/2004 | Dell |
| 2005/0002981 A1 | 1/2005 | Lahtinen |
| 2005/0021085 A1 | 1/2005 | Abrams |
| 2005/0059996 A1 | 3/2005 | Bauman |
| 2005/0059997 A1 | 3/2005 | Bauman |
| 2005/0070929 A1 | 3/2005 | Dalessandro |
| 2005/0118435 A1 | 6/2005 | DeLucia |
| 2005/0149073 A1 | 7/2005 | Arani |
| 2006/0004407 A1 | 1/2006 | Hiles |
| 2006/0135992 A1 | 6/2006 | Bettuchi |
| 2006/0173470 A1 | 8/2006 | Oray |
| 2006/0178683 A1 | 8/2006 | Shimoji |
| 2006/0271104 A1 | 11/2006 | Viola |
| 2007/0026031 A1 | 2/2007 | Bauman |
| 2007/0034669 A1 | 2/2007 | de la Torre |
| 2007/0049953 A2 | 3/2007 | Shimoji |
| 2007/0123839 A1 | 5/2007 | Rousseau |
| 2007/0179528 A1 | 8/2007 | Soltz |
| 2007/0203509 A1 | 8/2007 | Bettuchi |
| 2007/0203510 A1 | 8/2007 | Bettuchi |
| 2007/0246505 A1 | 10/2007 | Pace-Floridia |
| 2008/0029570 A1 | 2/2008 | Shelton |
| 2008/0082126 A1 | 4/2008 | Murray |
| 2008/0110959 A1 | 5/2008 | Orban |
| 2008/0125812 A1 | 5/2008 | Zubik |
| 2008/0140115 A1 | 6/2008 | Stopek |
| 2008/0161831 A1 | 7/2008 | Bauman |
| 2008/0161832 A1 | 7/2008 | Bauman |
| 2008/0169327 A1 | 7/2008 | Shelton |
| 2008/0169328 A1 | 7/2008 | Shelton |
| 2008/0169329 A1 | 7/2008 | Shelton |
| 2008/0169330 A1 | 7/2008 | Shelton |
| 2008/0169331 A1 | 7/2008 | Shelton |
| 2008/0169332 A1 | 7/2008 | Shelton |
| 2008/0169333 A1 | 7/2008 | Shelton |
| 2008/0200949 A1 | 8/2008 | Hiles |
| 2008/0290134 A1 | 11/2008 | Bettuchi |
| 2008/0308608 A1 | 12/2008 | Prommersberger |
| 2008/0314960 A1 | 12/2008 | Marczyk |
| 2009/0001121 A1 | 1/2009 | Hess |
| 2009/0001122 A1 | 1/2009 | Prommersberger |
| 2009/0001123 A1 | 1/2009 | Morgan |
| 2009/0001124 A1 | 1/2009 | Hess |
| 2009/0001125 A1 | 1/2009 | Hess |
| 2009/0001126 A1 | 1/2009 | Hess |
| 2009/0001128 A1 | 1/2009 | Weisenburgh, II |
| 2009/0001130 A1 | 1/2009 | Hess |
| 2009/0005808 A1 | 1/2009 | Hess |
| 2009/0030452 A1 | 1/2009 | Bauman |
| 2009/0043334 A1 | 2/2009 | Bauman |
| 2009/0076510 A1 | 3/2009 | Bell |
| 2009/0076528 A1 | 3/2009 | Sgro |
| 2009/0078739 A1 | 3/2009 | Viola |
| 2009/0095791 A1 | 4/2009 | Eskaros |
| 2009/0095792 A1 | 4/2009 | Bettuchi |
| 2009/0120994 A1 | 5/2009 | Murray |
| 2009/0134200 A1 | 5/2009 | Tarinelli |
| 2009/0206125 A1 | 8/2009 | Huitema |
| 2009/0206126 A1 | 8/2009 | Huitema |
| 2009/0206139 A1 | 8/2009 | Hall |
| 2009/0206141 A1 | 8/2009 | Huitema |
| 2009/0206142 A1 | 8/2009 | Huitema |
| 2009/0206143 A1 | 8/2009 | Huitema |
| 2009/0218384 A1 | 9/2009 | Aranyi |
| 2009/0277947 A1 | 11/2009 | Viola |
| 2009/0287230 A1 | 11/2009 | D'Agostino |
| 2010/0012704 A1 * | 1/2010 | Tarinelli Racenet et al. .............. 227/180.1 |
| 2010/0065606 A1 | 3/2010 | Stopek |
| 2010/0065607 A1 | 3/2010 | Orban, III |
| 2010/0072254 A1 * | 3/2010 | Aranyi et al. ............ 227/176.1 |
| 2010/0147921 A1 * | 6/2010 | Olson ...................... 227/175.1 |
| 2010/0147922 A1 | 6/2010 | Olson |
| 2010/0147923 A1 | 6/2010 | D'Agostino |
| 2010/0243707 A1 * | 9/2010 | Olson et al. ............. 227/176.1 |
| 2010/0243708 A1 * | 9/2010 | Aranyi et al. ............ 227/176.1 |

(56) References Cited

U.S. PATENT DOCUMENTS

| | | | |
|---|---|---|---|
| 2010/0243711 A1* | 9/2010 | Olson et al. | 227/181.1 |
| 2010/0249805 A1* | 9/2010 | Olson et al. | 606/144 |
| 2010/0264195 A1 | 10/2010 | Bettuchi | |
| 2010/0282815 A1 | 11/2010 | Bettuchi | |
| 2011/0024476 A1 | 2/2011 | Bettuchi | |
| 2011/0024481 A1 | 2/2011 | Bettuchi | |
| 2011/0036894 A1 | 2/2011 | Bettuchi | |
| 2011/0042442 A1 | 2/2011 | Viola | |
| 2011/0046650 A1 | 2/2011 | Bettuchi | |
| 2011/0057016 A1 | 3/2011 | Bettuchi | |
| 2011/0087279 A1* | 4/2011 | Shah et al. | 606/219 |
| 2011/0215132 A1 | 9/2011 | Aranyi | |
| 2012/0074199 A1 | 3/2012 | Olson | |
| 2012/0080336 A1 | 4/2012 | Shelton | |
| 2012/0187179 A1* | 7/2012 | Gleiman | 227/176.1 |
| 2012/0241499 A1 | 9/2012 | Baxter | |
| 2012/0273547 A1 | 11/2012 | Hodgkinson | |
| 2013/0037596 A1 | 2/2013 | Bear | |
| 2013/0098966 A1* | 4/2013 | Kostrzewski et al. | 227/176.1 |
| 2013/0105548 A1 | 5/2013 | Hodgkinson | |
| 2013/0105553 A1 | 5/2013 | Racenet | |
| 2013/0112732 A1* | 5/2013 | Aranyi et al. | 227/176.1 |
| 2013/0112733 A1* | 5/2013 | Aranyi et al. | 227/176.1 |
| 2013/0146641 A1 | 6/2013 | Shelton | |
| 2013/0153633 A1 | 6/2013 | Casasanta | |
| 2013/0153634 A1 | 6/2013 | Carter | |
| 2013/0153635 A1 | 6/2013 | Hodgkinson | |
| 2013/0153636 A1 | 6/2013 | Shelton | |
| 2013/0153638 A1 | 6/2013 | Carter | |
| 2013/0153639 A1 | 6/2013 | Hodgkinson | |
| 2013/0153640 A1 | 6/2013 | Hodgkinson | |
| 2013/0153641 A1 | 6/2013 | Shelton | |
| 2013/0161374 A1 | 6/2013 | Swayze | |
| 2013/0181031 A1* | 7/2013 | Olson et al. | 227/176.1 |
| 2013/0193186 A1 | 8/2013 | Racenet | |
| 2013/0193190 A1 | 8/2013 | Carter | |
| 2013/0193191 A1 | 8/2013 | Stevenson | |
| 2013/0193192 A1 | 8/2013 | Casasanta | |
| 2013/0209659 A1 | 8/2013 | Racenet | |
| 2013/0221062 A1 | 8/2013 | Hodgkinson | |
| 2013/0240600 A1 | 9/2013 | Bettuchi | |
| 2013/0240601 A1 | 9/2013 | Bettuchi | |
| 2013/0240602 A1 | 9/2013 | Stopek | |
| 2013/0274722 A1* | 10/2013 | Kostrzewski et al. | 606/1 |
| 2013/0277411 A1 | 10/2013 | Hodgkinson | |
| 2013/0306707 A1 | 11/2013 | Viola | |
| 2013/0310873 A1 | 11/2013 | Prommersberger | |
| 2013/0327807 A1 | 12/2013 | Olson | |
| 2014/0012317 A1 | 1/2014 | Orban | |
| 2014/0021242 A1 | 1/2014 | Hodgkinson | |
| 2014/0027490 A1 | 1/2014 | Marczyk | |
| 2014/0034704 A1 | 2/2014 | Ingmanson | |
| 2014/0048580 A1 | 2/2014 | Merchant | |
| 2014/0061280 A1 | 3/2014 | Ingmanson | |
| 2014/0061281 A1 | 3/2014 | Hodgkinson | |
| 2014/0084042 A1 | 3/2014 | Stopek | |
| 2014/0097224 A1 | 4/2014 | Prior | |
| 2014/0117066 A1 | 5/2014 | Aranyi | |
| 2014/0130330 A1 | 5/2014 | Olson | |
| 2014/0131418 A1 | 5/2014 | Kostrzewski | |
| 2014/0131419 A1 | 5/2014 | Bettuchi | |
| 2014/0138423 A1 | 5/2014 | Whitfield | |
| 2014/0151431 A1 | 6/2014 | Hodgkinson | |
| 2014/0155916 A1 | 6/2014 | Hodgkinson | |
| 2014/0158742 A1 | 6/2014 | Stopek | |
| 2014/0166721 A1 | 6/2014 | Stevenson | |
| 2014/0197224 A1 | 7/2014 | Penna | |
| 2014/0203061 A1 | 7/2014 | Hodgkinson | |
| 2014/0217147 A1 | 8/2014 | Milliman | |
| 2014/0217148 A1 | 8/2014 | Penna | |
| 2014/0239046 A1 | 8/2014 | Milliman | |
| 2014/0239047 A1 | 8/2014 | Hodgkinson | |

FOREIGN PATENT DOCUMENTS

| | | |
|---|---|---|
| EP | 0 594 148 | 4/1994 |
| EP | 0 327 022 | 4/1995 |
| EP | 0 667 119 | 8/1995 |
| EP | 1 064 883 | 1/2001 |
| EP | 1 256 317 | 11/2002 |
| EP | 1 256 318 | 11/2002 |
| EP | 1 520 525 | 4/2005 |
| EP | 1 621 141 | 2/2006 |
| EP | 1 702 570 | 9/2006 |
| EP | 1 759 640 | 3/2007 |
| EP | 1 815 804 | 8/2007 |
| EP | 1 825 820 | 8/2007 |
| EP | 1 929 958 | 6/2008 |
| EP | 1 994 890 | 11/2008 |
| EP | 2 005 894 | 12/2008 |
| EP | 2 005 895 | 12/2008 |
| EP | 2 008 595 | 12/2008 |
| EP | 2 090 231 | 8/2009 |
| EP | 2 090 244 | 8/2009 |
| EP | 2 090 252 | 8/2009 |
| EP | 2 198 787 | 6/2010 |
| EP | 2 236 098 | 10/2010 |
| EP | 2 236 099 | 10/2010 |
| EP | 2 311 386 | 4/2011 |
| EP | 2 436 348 | 4/2012 |
| EP | 2 462 880 | 6/2012 |
| EP | 2 517 637 | 10/2012 |
| EP | 2 586 380 | 5/2013 |
| EP | 2 604 195 | 6/2013 |
| EP | 2 604 197 | 6/2013 |
| EP | 2 620 106 | 7/2013 |
| EP | 2 630 922 | 8/2013 |
| EP | 2 644 125 | 10/2013 |
| JP | 2000-166933 | 6/2000 |
| JP | 2002-202213 | 7/2002 |
| JP | 2007-124166 | 5/2007 |
| WO | WO 90/05489 | 5/1990 |
| WO | WO 95/16221 | 6/1995 |
| WO | WO 96/22055 | 7/1996 |
| WO | WO 97/01989 | 1/1997 |
| WO | WO 97/13463 | 4/1997 |
| WO | WO 98/17180 | 4/1998 |
| WO | WO 99/45849 | 9/1999 |
| WO | WO 03/082126 | 10/2003 |
| WO | WO 03/088845 | 10/2003 |
| WO | WO 03/094743 | 11/2003 |
| WO | WO 03/105698 | 12/2003 |
| WO | WO 2005/079675 | 9/2005 |
| WO | WO 2006/023578 | 3/2006 |
| WO | WO 2006/044490 | 4/2006 |
| WO | WO 2006/083748 | 8/2006 |
| WO | WO 2007/121579 | 11/2007 |
| WO | WO 2008/057281 | 5/2008 |
| WO | WO 2008/109125 | 9/2008 |
| WO | WO 2010/075298 | 7/2010 |
| WO | WO 2011/143183 | 11/2011 |
| WO | WO 2012/044848 | 4/2012 |

OTHER PUBLICATIONS

European Search Report corresponding to EP 06 00 4598, completed Jun. 22, 2006; (2 pp).

European Search Report corresponding to EP 06 01 6962.0, completed Jan. 3, 2007 and mailed Jan. 11, 2007; (10 pp).

International Search Report corresponding to International Application No. PCT/US2005/036740, completed Feb. 20, 2007 and mailed Mar. 23, 2007; (8 pp).

International Search Report corresponding to International Application No. PCT/US2007/022713, completed Apr. 21, 2008 and mailed May 15, 2008; (1 p).

International Search Report corresponding to International Application No. PCT/US2008/002981, completed Jun. 9, 2008 and mailed Jun. 26, 2008; (2 pp).

European Search Report corresponding to EP 08 25 1779, completed Jul. 14, 2008 and mailed Jul. 23, 2008; (5 pp).

European Search Report corresponding to EP 08 25 1989.3, completed Mar. 11, 2010 and mailed Mar. 24, 2010; (6 pp).

(56) References Cited

OTHER PUBLICATIONS

European Search Report corresponding to EP 10 25 0639.1, completed Jun. 17, 2010 and mailed Jun. 28, 2010; (7 pp).
European Search Report corresponding to EP 10 25 0715.9, completed Jun. 30, 2010 and mailed Jul. 20, 2010; (3 pp).
European Search Report corresponding to EP 05 80 4382.9, completed Oct. 5, 2010 and mailed Oct. 12, 2010; (3 pp).
European Search Report corresponding to EP 10 25 1437.9, completed Nov. 22, 2010 and mailed Dec. 16, 2010; (3 pp).
European Search Report corresponding to EP 09 25 2897.5, completed Feb. 7, 2011 and mailed Feb. 15, 2011; (3 pp).
European Search Report corresponding to EP 10 25 0642.5, completed Mar. 25, 2011 and mailed Apr. 4, 2011; (4 pp).
European Search Report corresponding to EP 11 18 8309.6, completed Dec. 15, 2011 and mailed Jan. 12, 2012; (3 pp).
European Search Report corresponding to EP 12 15 2229.6, completed Feb. 23, 2012 and mailed Mar. 1, 2012; (4 pp).
European Search Report corresponding to EP 12 15 0511.9, completed Apr. 16, 2012 and mailed Apr. 24, 2012; (7 pp).
European Search Report corresponding to EP 12 15 2541.4, completed Apr. 23, 2012 and mailed May 3, 2012; (10 pp).
European Search Report corresponding to EP 12 16 5609.4, completed Jul. 5, 2012 and mailed Jul. 13, 2012; (8 pp).
European Search Report corresponding to EP 12 15 8861.0, completed Jul. 17, 2012 and mailed Jul. 24, 2012; (9 pp).
European Search Report corresponding to EP 12 16 5878.5, completed Jul. 24, 2012 and mailed Aug. 6, 2012; (8 pp).
Extended European Search Report corresponding to EP 12 19 1035.0, completed Jan. 11, 2013 and mailed Jan. 18, 2013; (7 pp).
Extended European Search Report corresponding to EP 12 18 6175.1, completed Jan. 15, 2013 and mailed Jan. 23, 2013; (7 pp).
Extended European Search Report corresponding to EP 12 19 1114.3, completed Jan. 23, 2013 and mailed Jan. 31, 2013; (10 pp).
Extended European Search Report corresponding to EP 12 19 2224.9, completed Mar. 14, 2013 and mailed Mar. 26, 2013; (8 pp).
Extended European Search Report corresponding to EP 12 19 6904.2, completed Mar. 28, 2013 and mailed Jul. 26, 2013; (8 pp).
Extended European Search Report corresponding to EP 12 19 6911.7, completed Apr. 18, 2013 and mailed Apr. 24, 2013; (8 pp).
Extended European Search Report corresponding to EP 07 00 5842.5, completed May 13, 2013 and mailed May 29, 2013; (7 pp).
Extended European Search Report corresponding to EP 12 19 8776.2, completed May 16, 2013 and mailed May 27, 2013; (8 pp).
Extended European Search Report corresponding to EP 12 19 8749.9, completed May 21, 2013 and mailed May 31, 2013; (8 pp).
Extended European Search Report corresponding to EP 13 15 6297.7, completed Jun. 4, 2013 and mailed Jun. 13, 20131; (7 pp).
Extended European Search Report corresponding to EP 13 17 3985.6, completed Aug. 19, 2013 and mailed Aug. 28, 2013; (6 pp).
Extended European Search Report corresponding to EP 13 17 3986.4, completed Aug. 20, 2013 and mailed Aug. 29, 2013; (6 pp).
Extended European Search Report corresponding to EP 13 17 7437.4, completed Sep. 11, 2013 and mailed Sep. 19, 2013; 6 pages.
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report corresponding to EP 08 72 6500.5, completed Feb. 20, 2014 and mailed Mar. 3, 2014; (7 pp).
Extended European Search Report corresponding to EP 13 19 5919.9, completed Feb. 10, 2014 and mailed Mar. 3, 2014; (7 pp).
Extended European Search Report corresponding to EP 13 19 2123.1, completed Jan. 30, 2014 and mailed Feb. 10, 2014; (8 pp).
Extended European Search Report corresponding to EP 13 19 6816.6, completed Mar. 28, 2014 and mailed Apr. 9, 2014; (9 pp).
Extended European Search Report corresponding to EP 13 19 4995.0, completed Jun. 5, 2014 and mailed Jun. 16, 2014; (5 pp).
Extended European Search Report corresponding to EP 13 19 5019.8, completed Mar. 14, 2014 and mailed Mar. 24, 2014; (7 pp).
Extended European Search Report corresponding to EP 13 19 2111.6, completed Feb. 13, 2014 and mailed Feb. 27, 2014; (10 pp).
Extended European Search Report corresponding to EP 13 19 7958.5, completed Apr. 4, 2014 and mailed Apr. 15, 2014; (8 pp).
Extended European Search Report corresponding to EP 14 15 6342.9, completed Jul. 22, 2014 and mailed Jul. 29, 2014; (8 pp).
Extended European Search Report corresponding to EP 14 15 7195.0, completed Jun. 5, 2014 and mailed Jun. 18, 2014; (9 pp).

\* cited by examiner

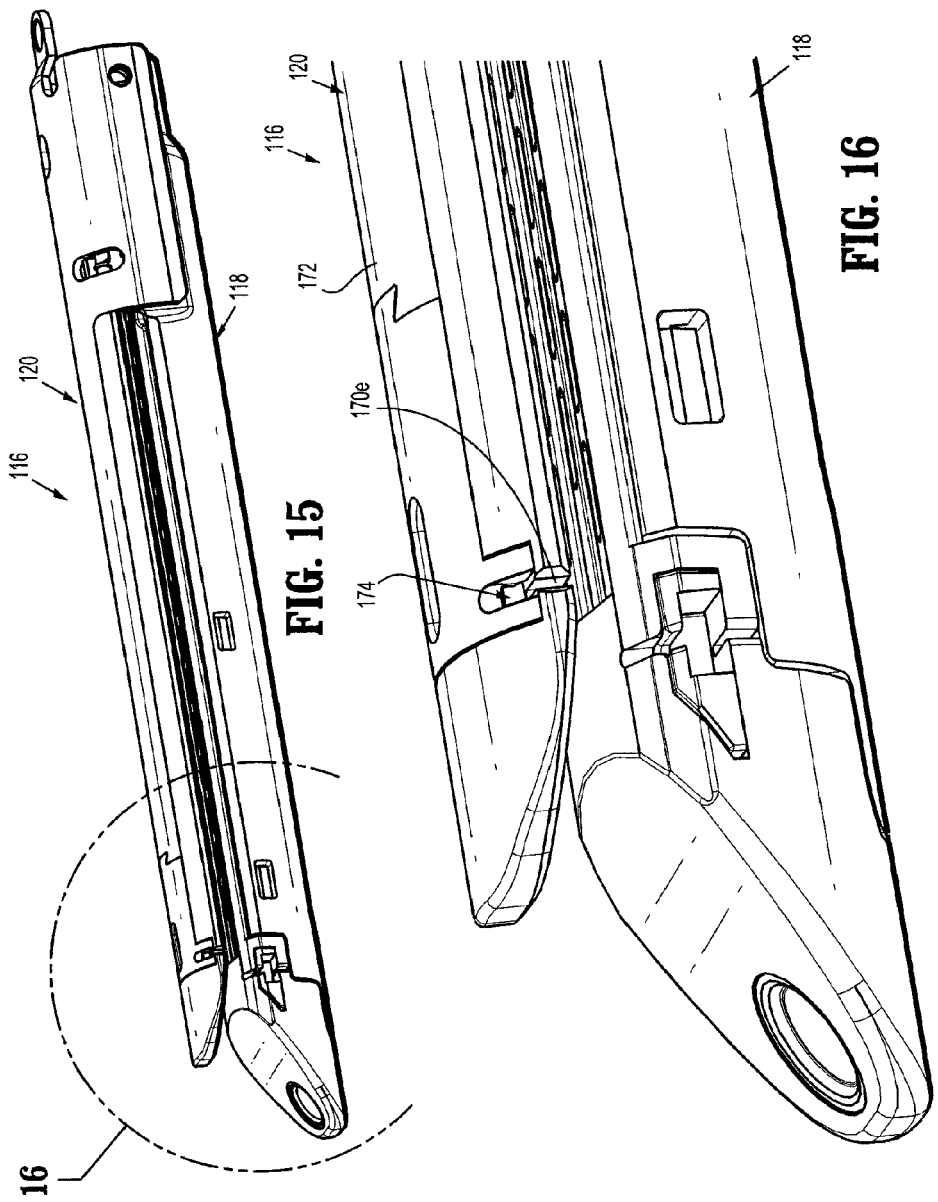

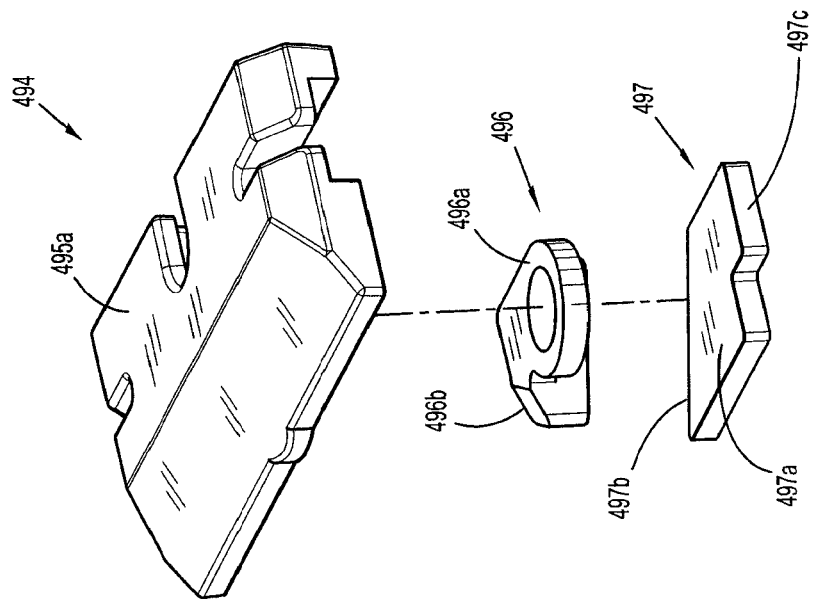
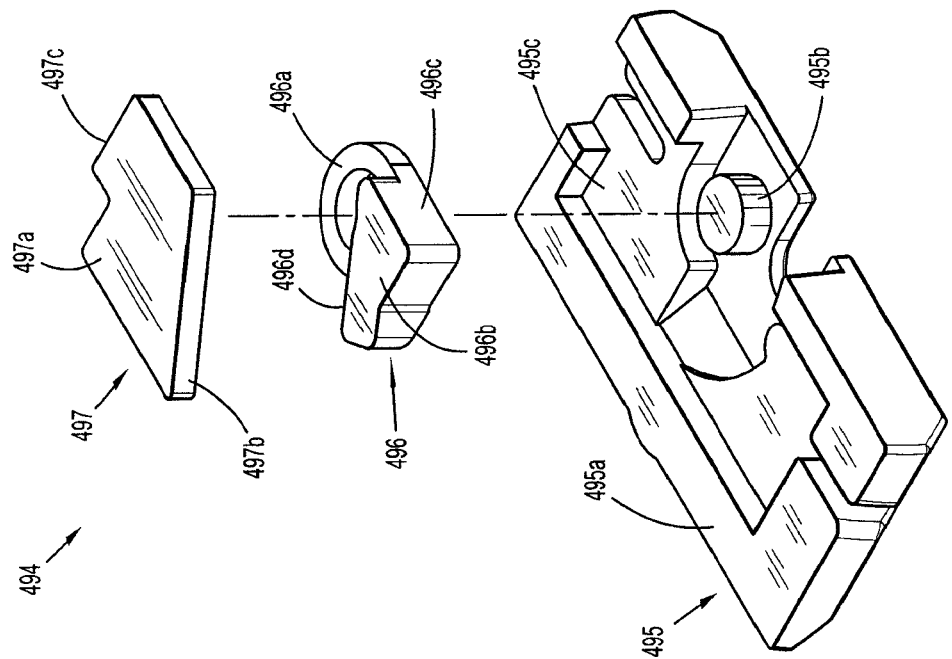

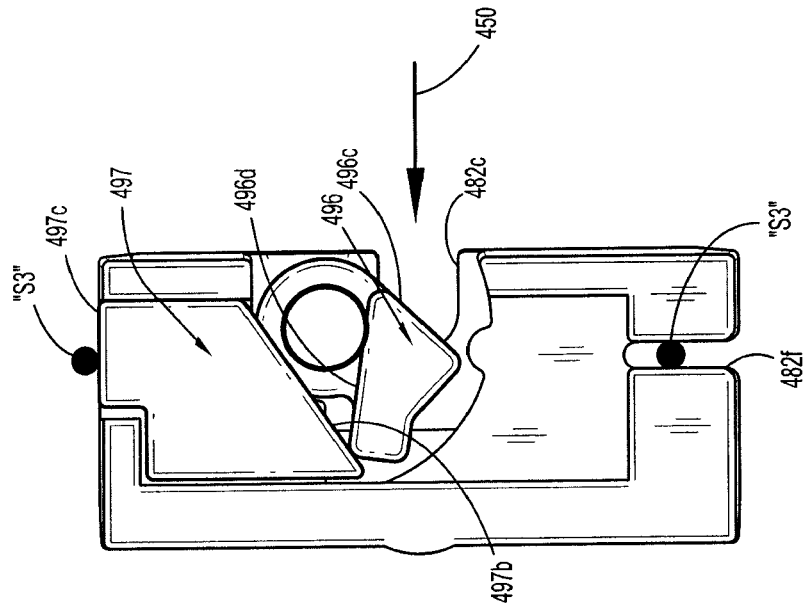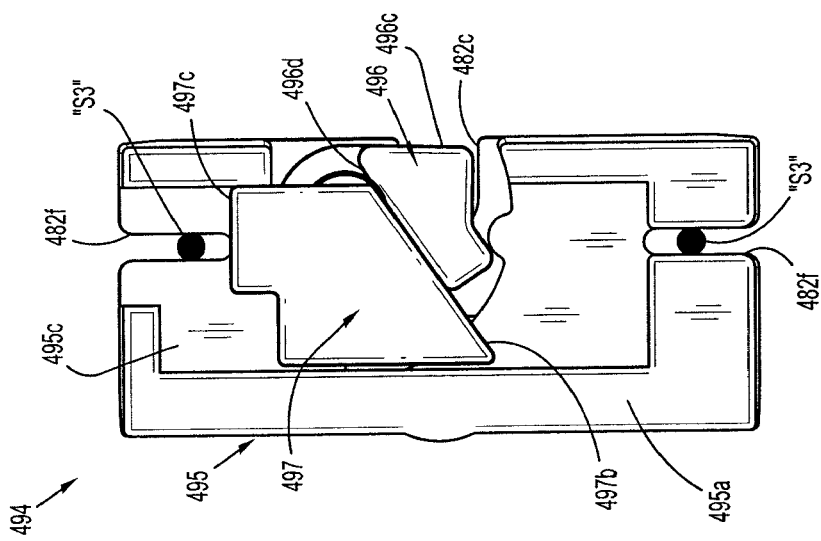

SURGICAL STAPLING APPARATUS

CROSS-REFERENCE TO RELATED APPLICATIONS

The present application is a Continuation application, which claims the benefit and priority to U.S. patent application Ser. No. 13/787,921, filed on Mar. 7, 2013, which is a Continuation of U.S. patent application Ser. No. 13/223,519, filed on Sep. 1, 2011, now U.S. Pat. No. 8,408,440, which is a Continuation of U.S. patent application Ser. No. 12/414,931, filed on Mar. 31, 2009, now U.S. Pat. No. 8,016,178, the entire content of each of which being incorporated herein by reference.

BACKGROUND

1. Technical Field

The present disclosure relates to a surgical apparatus having a buttress material incorporated therewith. More particularly, the present disclosure relates to a surgical stapling apparatus including a detachable surgical buttress and/or an endoscopic surgical stapling apparatus that includes a detachable surgical buttress.

2. Background of Related Art

Surgical devices for grasping or clamping tissue between opposing jaw structure and then joining tissue by surgical fasteners are well known in the art. In some instruments a knife is provided to cut the tissue which has been joined by the fasteners. The fasteners are typically in the form of surgical staples but two-part polymeric fasteners can also be utilized.

Instruments for this purpose can include two elongated jaw members which are respectively used to capture or clamp tissue. In certain surgical staplers, one of the jaw members carries a staple cartridge which houses a plurality of staples arranged in at least two lateral rows while the other jaw member has an anvil that defines a surface for forming the staple legs as the staples are driven from the staple cartridge. The stapling operation is effected by cam members that travel longitudinally through the staple cartridge, with the cam members acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. No. 3,079,606 and U.S. Pat. No. 3,490,675.

Another stapler disclosed in U.S. Pat. No. 3,499,591 also applies a double row of staples on each side of the incision. This patent discloses a surgical stapler that has a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. Other examples of such staplers are disclosed in U.S. Pat. Nos. 4,429,695 and 5,065,929.

Each of the instruments described above is designed for use in surgical procedures in which surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); U.S. Pat. No. 5,332,142 (Robinson, et al.); and U.S. Pat. No. 6,241,139 (Milliman et al.), the entire contents of each of which are hereby incorporated herein by reference.

Tyco Healthcare Group, LP, the assignee of the present application, has manufactured and marketed endoscopic stapling instruments, such as the Multifire ENDO GIA™ 30 and Multifire ENDO GIA™ 60 instruments, for a number of years. These instruments include a surgical stapling apparatus and a loading unit. Typically, the loading unit is attached to the apparatus immediately prior to surgery. After use, the loading unit can be removed from the apparatus and a new loading unit can be fastened to the apparatus to perform additional stapling and/or cutting operations. These instruments have provided significant clinical benefits. Nonetheless, improvements to these instruments are still desirable.

When stapling relatively thin or fragile tissues, it is important to effectively seal the staple line against air or fluid leakage. Additionally, it is often necessary to reinforce the staple line against the tissue to prevent tears in the tissue or pulling of the staples through the tissue. One method of preventing tears or pull through involves the placement of a biocompatible fabric reinforcing material, or "buttress" material, between the staple and the underlying tissue. In this method, a layer of buttress material is placed against the tissue and the tissue is stapled in conventional manner. In another method, the buttress material is positioned on the stapling instrument itself prior to stapling the tissue. An exemplary example of this is disclosed in U.S. Pat. No. 5,542,594 to McKean et al., the entire content of which is incorporated herein by reference. In McKean et al., a tube of buttress material is slipped over the jaw of the stapler. The stapler is then actuated to staple the subject tissue and secure the buttress material between the tissue and staple line to reinforce the tissue and staple line.

SUMMARY

In accordance with the present disclosure a surgical stapling apparatus is provided including a housing; a handle supported by the housing; an elongated body extending distally from the housing; and a tool assembly at the distal end of the elongated body. The tool assembly has a cartridge assembly including a cartridge having a plurality of surgical fasteners therein, and an anvil assembly, wherein at least one of the cartridge assembly and anvil assembly being movable in relation to the other of the cartridge assembly and anvil assembly, wherein the anvil assembly includes an anvil plate, and wherein each of the anvil plate and the staple cartridge define an elongate longitudinal slot. The surgical stapling apparatus further includes a surgical buttress releasably secured to a tissue contacting surface of at least one of the anvil plate and the staple cartridge, wherein each surgical buttress is secured to the at least one of the anvil assembly and the cartridge assembly by at least one anchor; a release assembly associated with the at least one of the anvil assembly and the cartridge assembly; and a drive assembly slidably translatable through the tool assembly from a proximal position to a distal position, wherein the drive assembly actuates the release assembly to thereby release the anchor and to free the surgical buttress from the at least one of the anvil assembly and cartridge assembly.

The release assembly may grip the at least one anchor prior to an actuation of the drive assembly.

The at least one of the anvil assembly and the cartridge assembly may define a side slot for receiving an end of the at least one anchor therein.

The release assembly may include a first bar extending across the longitudinal slot prior to an actuation of the drive assembly; and a second bar, connected to and actuatable by the first bar, having an end extending at least partially into the side slot, prior to an actuation of the drive assembly.

In use, as the drive assembly is advanced to the distal position, the drive assembly may actuate the first bar of the release assembly which in turn may actuate the second bar of the release assembly to release the anchor disposed within the side slot.

Each of the anvil assembly and the cartridge assembly may include a release assembly. Each of the anvil assembly and the cartridge assembly may define a side slot for receiving the anchor of each surgical buttress.

Each release assembly may include a first bar extending across the longitudinal slot prior to an actuation of the drive assembly; and a second bar, connected to and actuatable by the first bar, having an end extending at least partially into the side slot, prior to an actuation of the drive assembly. In use, as the drive assembly is advanced to the distal position, the drive assembly may actuate the first bar of each release assembly which in turn may actuate the second bar of each release assembly to release the anchor disposed within the each side slot.

At least one of the anvil assembly and the cartridge assembly may include a constricting, open-ended, side slot configured to grip an end of the anchor, and wherein the release assembly may push the end of the anchor out of the side slot, upon a distal advancement of the drive assembly.

The release assembly may include a pusher that is in operative association with the side slot retaining the end of the anchor. The pusher may be actuatable by a distally advancing drive member to push the end of the anchor out of the side slot.

The pusher of the release assembly may be one of pivotally connected to and slidably supported in at least one of the anvil assembly and the cartridge assembly.

The anchor may be a suture engaging the surgical buttress and the at least one of the cartridge assembly and the anvil assembly. The anchor may be an extension of the surgical buttress and engages the at least one of the cartridge assembly and the anvil assembly.

According to another aspect of the present application, a loading unit for use with a surgical stapling apparatus is provided and includes a tool assembly having a cartridge assembly including a cartridge having a plurality of surgical fasteners therein, and an anvil assembly, at least one of the cartridge assembly and the anvil assembly being movable in relation to the other of the cartridge assembly and anvil assembly, wherein the anvil assembly includes an anvil plate and, wherein each of the anvil plate and the staple cartridge define an elongate longitudinal slot; a surgical buttress releasably secured to a tissue contacting surface of at least one of the anvil plate and the staple cartridge, wherein each surgical buttress is secured to the at least one of the anvil assembly and the cartridge assembly by at least one anchor; a release assembly associated with the at least one of the anvil assembly and the cartridge assembly; and a drive assembly slidably translatable through the tool assembly from a proximal position to a distal position, the drive assembly actuating the release assembly to thereby release the anchor to free the surgical buttress from the at least one of the anvil assembly and cartridge assembly.

The release assembly may grip the at least one anchor prior to an actuation of the drive assembly.

At least one of the anvil assembly and the cartridge assembly may define a side slot for receiving an end of the at least one anchor therein.

The release assembly may include a first bar extending across the longitudinal slot prior to an actuation of the drive assembly; and a second bar, connected to and actuatable by the first bar, having an end extending at least partially into the side slot, prior to an actuation of the drive assembly.

In use, as the drive assembly is advanced to the distal position, drive assembly actuates the first bar of the release assembly which in turn actuates the second bar of the release assembly to release the grip on the end of the at least one anchor disposed within the side slot.

Each of the anvil assembly and the cartridge assembly may include a release assembly.

At least one of the anvil assembly and the cartridge assembly may include a constricting, open-ended, side slot configured to grip an end of the anchor disposed therein, and wherein the release assembly may push the end of the anchor out of the side slot, upon a distal advancement of the drive assembly.

Additional advantages will become apparent from the description which follows, taken in conjunction with the accompanying drawings.

BRIEF DESCRIPTION OF THE DRAWINGS

The present disclosure will be further described with reference to the accompanying drawings, wherein like reference numerals refer to like parts in the several views, and wherein:

FIG. 15 is a perspective view of a distal end of a loading unit including suture release assemblies according to another embodiment of the present disclosure;

FIG. 16 is an enlarged view of the indicated area of detail of FIG. 15;

FIG. 35 is a bottom, perspective view, with parts separated, of the suture release assembly of FIGS. 32-34;

FIG. 36 is a top, perspective view, with parts separated, of the suture release assembly of FIGS. 32-35;

FIG. 37 is a top, plan view of the suture release assembly of FIGS. 32-36, illustrating the suture release assembly in an unactuated configuration; and FIG. 38 is a top, plan view of the suture release assembly of FIGS. 32-37, illustrating the suture release assembly in an actuated configuration.

DETAILED DESCRIPTION OF EMBODIMENTS

Figure 1:
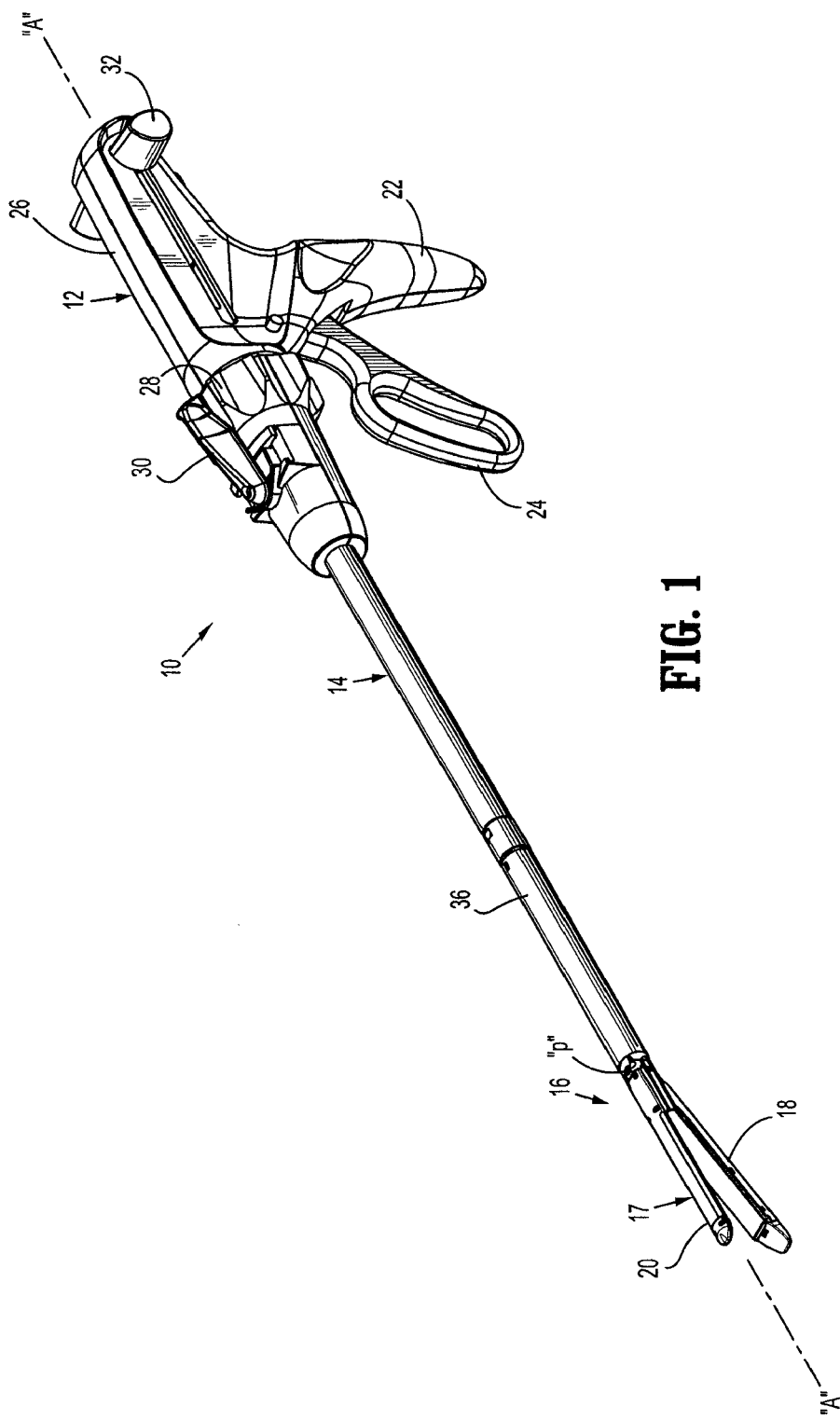
FIG. 1 is a perspective view of a surgical stapling apparatus according to an embodiment of the present disclosure.

Embodiments of the presently disclosed surgical stapling apparatus and loading unit will now be described in detail with reference to the drawings, in which like reference numerals designate identical or corresponding elements in each of the several views.

In the drawings and in the description that follows, the term "proximal", as is traditional, will refer to the end of the stapling apparatus which is closest to the operator, while the term "distal" will refer to the end of the apparatus which is furthest from the operator.

FIG. 1 shows a surgical apparatus, e.g., surgical stapling apparatus, generally referred to as 10. In the interest of brevity, this disclosure will focus primarily on to the tool assembly of the surgical stapling apparatus 10. A detailed discussion of the remaining components and method of use of surgical stapling apparatus 10 is disclosed in U.S. Pat. No. 6,241,139, the disclosure of which is hereby incorporated by reference herein.

Surgical stapling apparatus 10 is an endoscopic apparatus and includes a handle assembly 12 and an elongated body 14 extending from handle assembly 12. A loading unit 16 is releasably secured to the distal end of elongated body 14. Furthermore, the present disclosure contemplates surgical stapling apparatus that have a replaceable cartridge that is received in the jaws of the apparatus.

Loading unit 16 includes a tool assembly 17 having a cartridge assembly 18 housing a plurality of surgical fasteners or staples 84 (see FIG. 2) and an anvil assembly 20 secured in juxtaposed relation relative to cartridge assembly 18, wherein anvil assembly 20 and cartridge assembly 18 are moveable to or away from one another to close or open tool assembly 17. As shown herein, loading unit 16 is configured to apply six (6) linear rows of staples, in loading units measuring from about 30 mm to about 60 mm in length. Loading units for applying any number of rows of staples, having staple pockets arranged in various patterns and/or loading units and end effectors having any other lengths, e.g., 45 mm, are also envisioned. Handle assembly 12 includes a stationary handle member 22, a movable handle member 24, and a barrel portion 26.

A rotatable member 28 is mounted on the forward end of barrel portion 26 to facilitate rotation of elongated body 14 and attached loading unit 16 with respect to handle assembly 12. An articulation lever 30 is also mounted on the forward end of barrel portion 26 adjacent rotatable member 28 to facilitate articulation of tool assembly 17. Preferably, a pair of knobs 32 are movably positioned along barrel portion 26. Knobs 32 are advanced distally to approximate or close cartridge and/or anvil assembly 18, 20, and retracted proximally to unapproximate or open cartridge and/or anvil assembly 18, 20.

Loading unit 16 is desirably selectively removably couplable to elongated body 14. Loading unit 16 includes a housing portion 36 having a proximal end adapted to releasably engage the distal end of elongated body 14. A mounting assembly 38 is pivotally secured at "P" to the distal end of housing portion 36, and is configured to receive the proximal end of tool assembly 17 such that pivotal movement of tool assembly 17 about an axis at "P", perpendicular to the longitudinal axis of housing portion 36, effects articulation of tool assembly 17.

Figure 2:
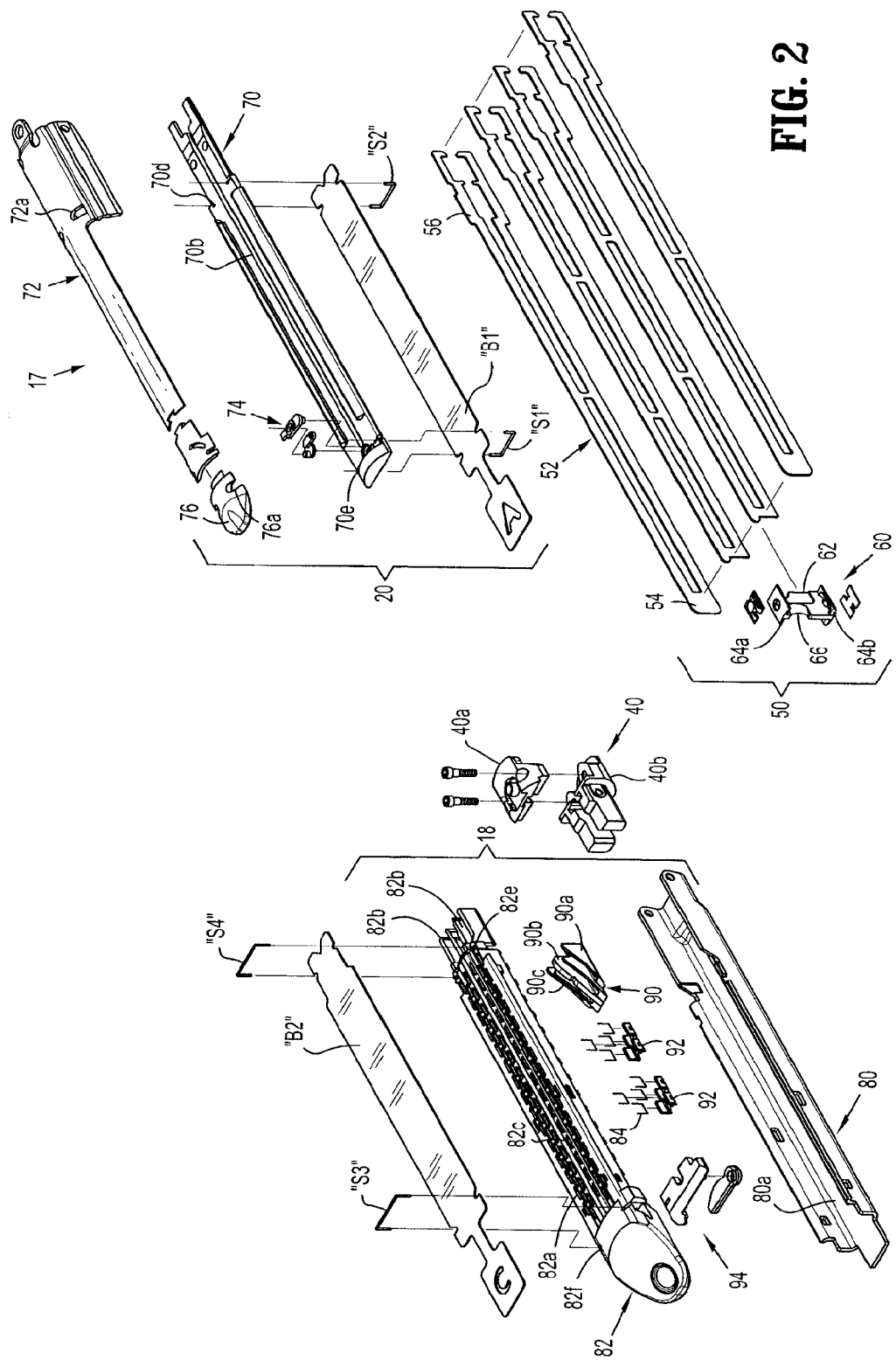
FIG. 2 is a top, perspective view, with parts separated, of a distal end of a loading unit of the surgical stapling apparatus of FIG. 1.

With general reference to FIG. 2, loading unit 16 includes a mounting assembly 40. Mounting assembly 40 includes an upper and a lower mounting portion 40a, 40b, respectively. An axial drive assembly 50 is operatively associated with and slidably disposed between cartridge and/or anvil assembly 18, 20. With reference to FIG. 2, axial drive assembly 50 includes an elongated drive beam 52 having a distal end 54 and a proximal end 56. Drive beam 52 may be constructed from a single sheet of material or, preferably, multiple stacked sheets.

Proximal end 56 of drive beam 52 of drive assembly 50 includes a pair of resilient engagement fingers that receive a pusher. The pusher is dimensioned and configured to mountingly engage a drive member, e.g., a drive rod or control rod (not shown) when the proximal end of loading unit 16 is engaged with elongated body 14 of surgical stapling apparatus 10. The control rod functions to impart axial movement of drive assembly 50 from handle assembly 12.

Distal end 54 of drive beam 52 of drive assembly 50 includes a head 60 with a laterally extending upper portion 64a, a laterally extending lower portion 64b, and a central wall portion 62. A distal edge of central wall portion 62 defines a knife blade or the like 66.

As seen in FIG. 2, anvil assembly 20 includes an anvil plate 70 having a plurality of staple deforming pockets/cavities (not shown) and a cover plate 72 secured to a top surface of anvil plate 70, having a cavity (not shown) is defined therebetween. The cavity defined between the anvil plate 70 and cover plate 72 is dimensioned to receive the upper portion 64a of head 60 therein. A longitudinal slot 70b extends through anvil plate 70 to facilitate passage of central wall portion 62 of head 60 therethrough. Additionally, cover plate 72 defines a pair of opposed recesses 72a formed therein which align with the proximal pair of recesses 70d formed in anvil plate 70 when cover plate 72 is assembled with anvil plate 70.

With continued reference to FIG. 2, anvil plate 70 defines a proximal pair of recesses 70d formed near a proximal end of anvil plate 70 and disposed, one each, on opposed sides of longitudinal slot 70b. Anvil plate 70 defines a distal pair of recesses 70e formed near a distal end of anvil plate 70 and disposed, one each, on opposed sides of longitudinal slot 70b. In one embodiment, at least one of the recesses of each of the proximal pair of recesses 70d and the distal pair of recesses 70e is preferably non-circular and constricting, or has a reduced width dimension, so as to frictionally engage and/or pinch an anchor "S".

As used herein the term anchor is understood to include and is not limited to sutures, threads, tethers, straps, bands, lines, wires, cables, fasteners, tacks or any other material suitable for the intended purpose disclosed herein. In certain embodiments, the anchor is an extension of the staple line reinforcement material discussed below. The anchor may comprise an integral part of the staple line reinforcement material, or may be formed from the same or a similar material and attached to the staple line reinforcement material.

Figure 2A:
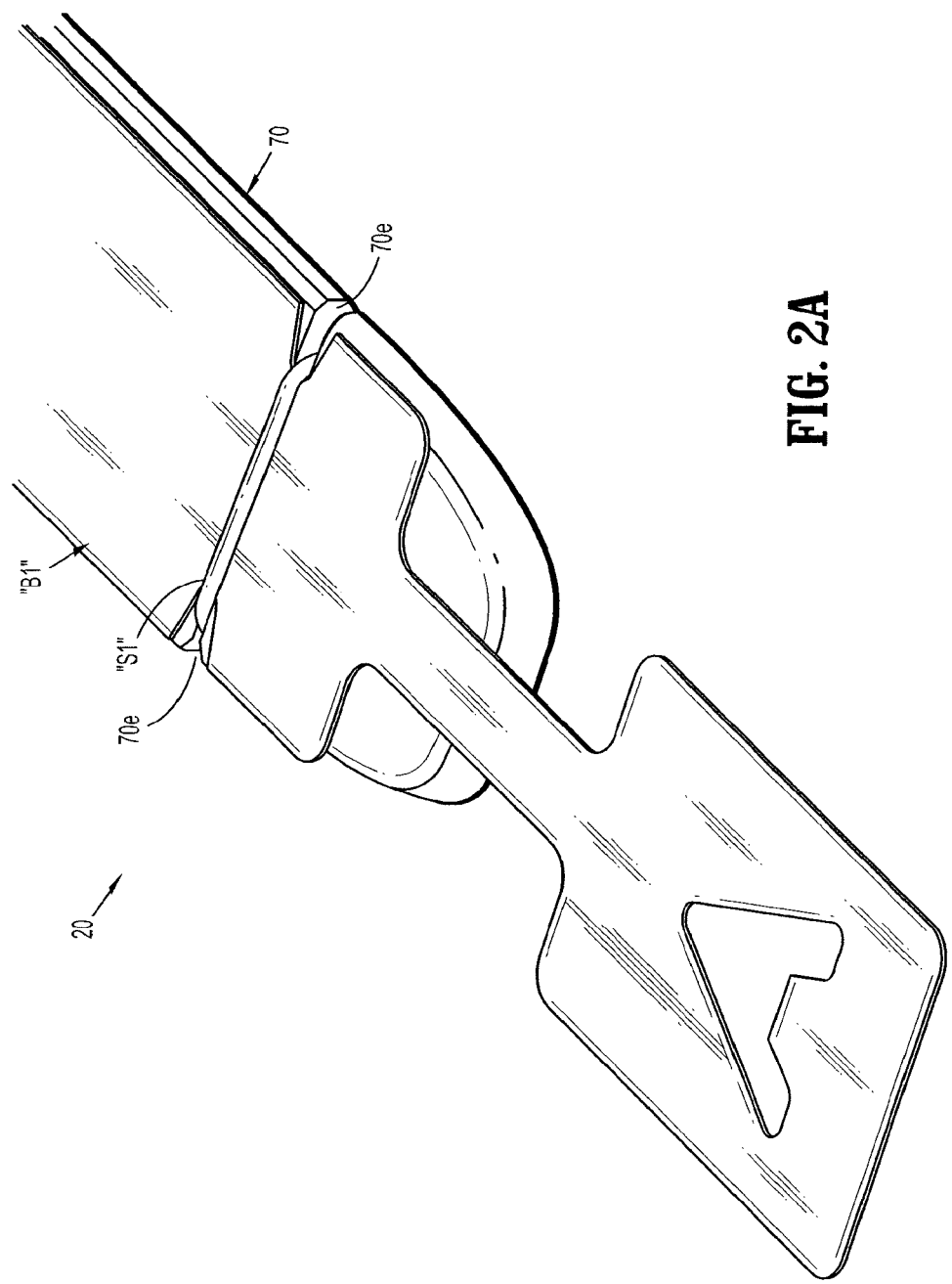
FIG. 2A is an enlarged perspective view of a distal end of an anvil assembly of the loading unit illustrating a surgical anvil buttress operatively secured to a tissue contacting surface thereof.

As seen in FIGS. 2 and 2A, anvil assembly 20 further includes a surgical anvil buttress "B1", pledget or the like operatively secured to a lower surface or tissue contacting surface of anvil plate 70, by an anchor "S", to overlie at least some of anvil pockets 70a and/or at least a portion of a length of longitudinal slot 70b. In particular, an anchor "S" is wrapped over a proximal portion of surgical anvil buttress "B1" and cinched in each of the proximal pair of recesses 70d and an anchor "S" is wrapped around a distal portion of the surgical anvil buttress "B1" and cinched in each of the distal pair of recesses 70e.

Surgical anvil buttress "B1" includes a proximal pair of notches formed in side edges aligned with the proximal pair of recesses 70d of anvil plate 70, a distal pair of notches formed in side edges thereof aligned with the distal pair of recesses 70e of anvil plate 70, and a proximal notch formed in a proximal edge thereof aligned with longitudinal slot 70b when surgical anvil buttress "B1" is secured to anvil assembly 20. Surgical anvil buttress "B1" further includes a tongue or tab extending from a distal edge thereof to facilitate with the attachment of surgical anvil buttress "B1" to anvil assembly 20 during the assembly process. It is contemplated that the tongue is removed from surgical anvil buttress "B1" following securement of surgical anvil buttress "B1" to anvil assembly 20 and prior to packaging or shipment.

As seen in FIGS. 2-9, anvil assembly 20 further includes a release assembly 74 disposed between anvil plate 70 and cover plate 72 at a location in operative registration with the distal pair of recesses 70e. Release assembly 74 includes a guide plate 75 defining an arcuate slot 75a formed therethrough. Slot 75a is configured and dimensioned to receive a tool (not shown) therethrough. The function and purpose of slot 75a will be discussed in greater detail below.

Figure 4:
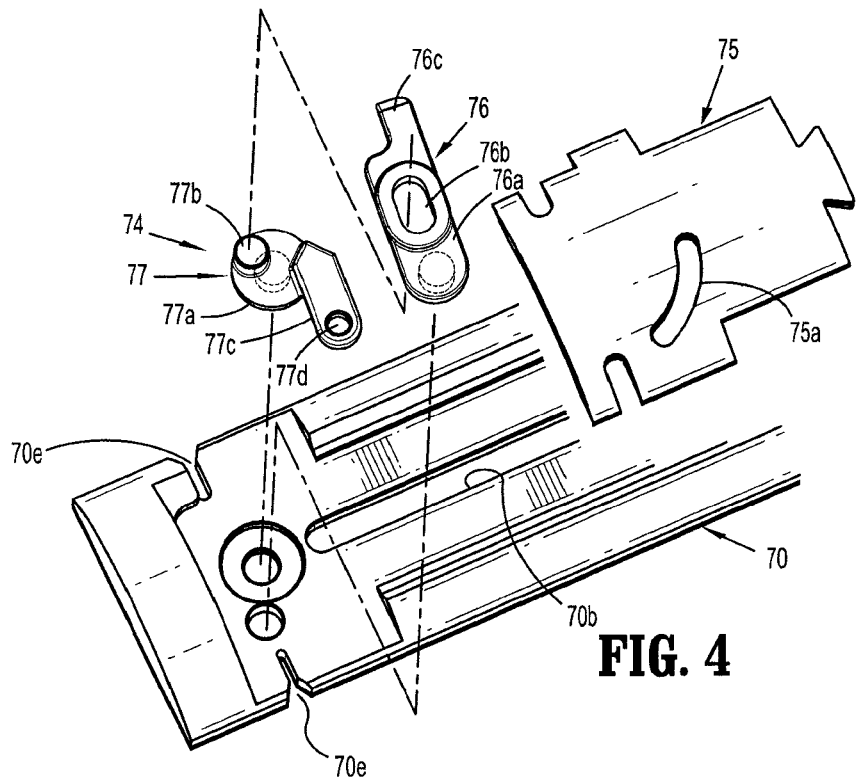
FIG. 4 is a top, perspective view of the anvil assembly of FIG. 3, illustrating the parts of the suture release assembly thereof separated.
Figure 5:
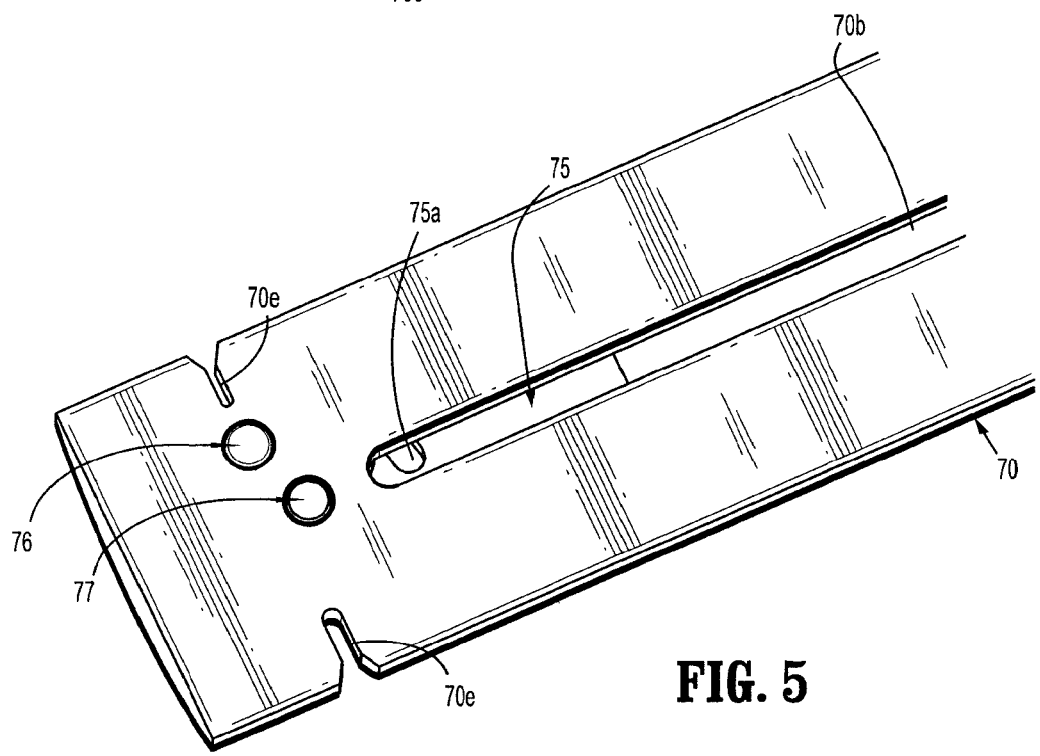
FIG. 5 is a bottom, perspective view of the anvil assembly of FIGS. 3 and 4.

Release assembly 74 further includes a lock or anchor bar 76 pivotally connected to anvil plate 70 (as seen in FIGS. 4 and 5) and/or optionally cover plate 72 (shown in FIG. 2). Anchor bar 76 includes a body portion 76a defining an elongate channel or slot 76b therein and a finger 76c extending from an edge thereof. Finger 76c is in operative registration with one of the distal pair of recesses 70e, preferably, the one of the distal pair of recesses having the relatively larger width dimension.

Suture release assembly 74 further includes an anchor bar actuation member 77 pivotally connected to anvil plate 70 (as seen in FIGS. 4 and 5) and/or optionally cover plate 72 (shown in FIG. 2). Actuation member 77 includes an eccentric cam 77a defining a central axis of rotation about which actuation member is permitted to rotate. Actuation member 77 includes a nub or boss 77b extending from a surface of eccentric cam 77a in a direction substantially parallel to and offset a radial distance from the central axis of rotation of eccentric cam 77a. Boss 77b is slidably and rotatably disposed in elongate slot 76b of anchor bar 76. Actuation member 77 further includes a release bar 77c extending substantially tangentially from eccentric cam 77a from a side substantially opposite to boss 77b. Release bar 77c defines a pin 77d formed thereon which is in registration with the arcuate slot 75a of guide plate 75. In operation, as eccentric cam 77a is rotated, pin 77d of release bar 77c follows along the path of arcuate slot 75a of guide plate 75.

Figure 6:
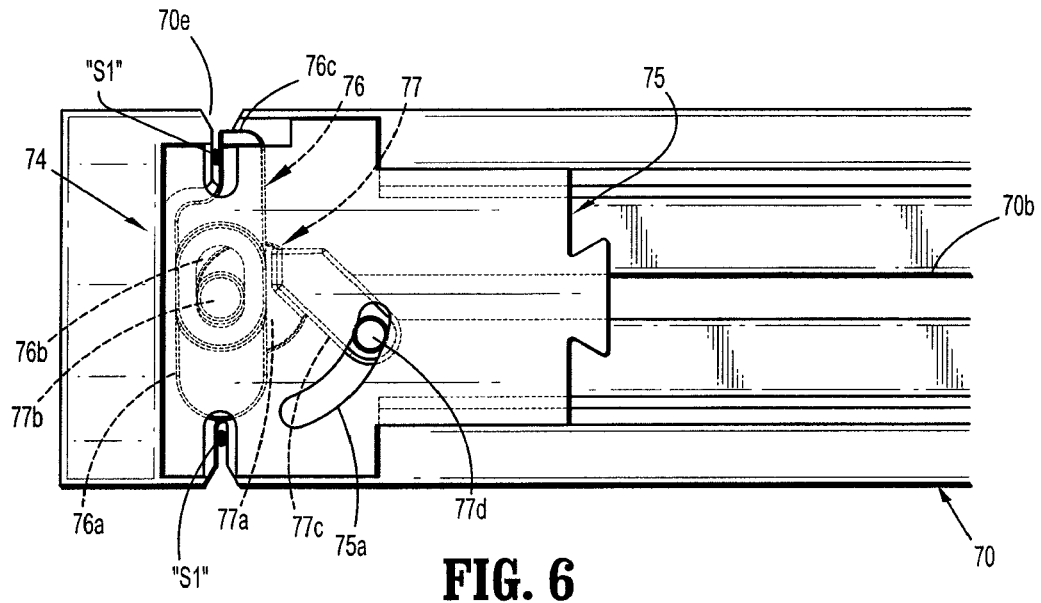
FIG. 6 is a top, plan view of the anvil assembly of FIGS. 3-5, illustrating the suture release assembly thereof in the closed configuration.
Figure 7:
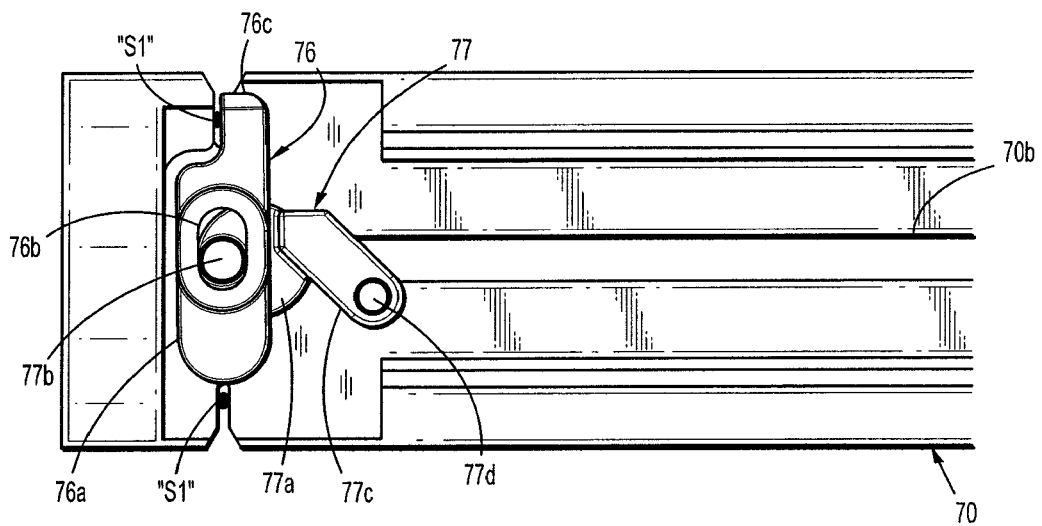
FIG. 7 is a top, plan view of the anvil assembly of FIG. 6, with a retainer removed therefrom.

As seen in FIGS. 6 and 7, suture release assembly 74 includes a locking or anchoring configuration wherein finger 76c of anchor bar 76 extends into or overlies the respective one of the pair of distal recesses 70e in operative registration therewith, release bar 77c of actuation member 77 extends across knife slot 70b of anvil plate 70, and pin 77d of release bar 77c is disposed at or near a first end of arcuate slot 75a of guide plate 75. It is contemplated that suture release assembly 74 may include a friction fit or snap fit feature for maintaining and/or retaining suture release assembly 74 in the locking or anchoring configuration at all times following the manufacturing/assembly process and prior to a complete firing of surgical stapling apparatus 10.

Figure 8:
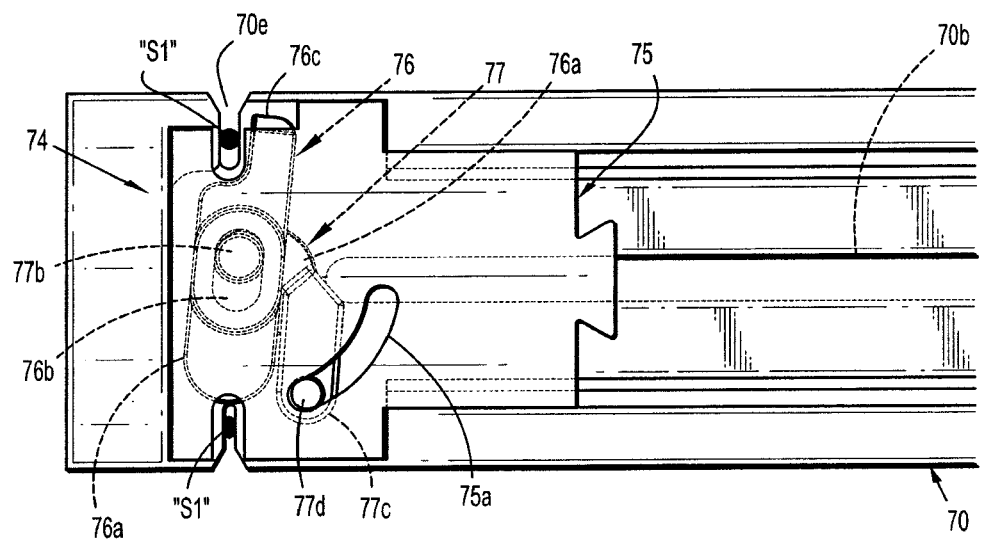
FIG. 8 is a top, plan view of the anvil assembly of FIGS. 3-7, illustrating the suture release assembly thereof in the open configuration.
Figure 9:
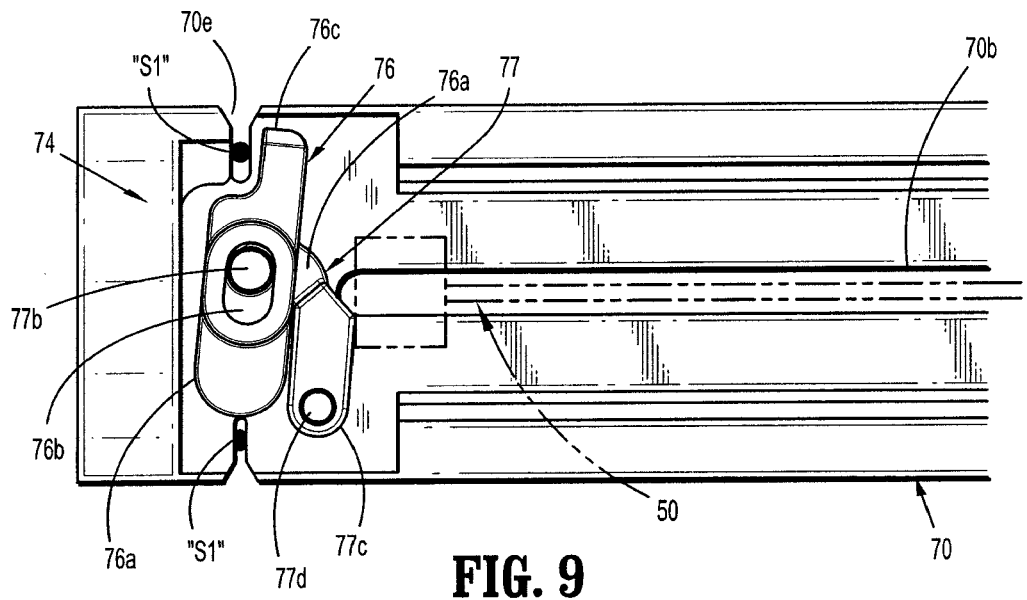
FIG. 9 is a top, plan view of the anvil assembly of FIG. 8, with a retainer removed therefrom.
Figure 10:
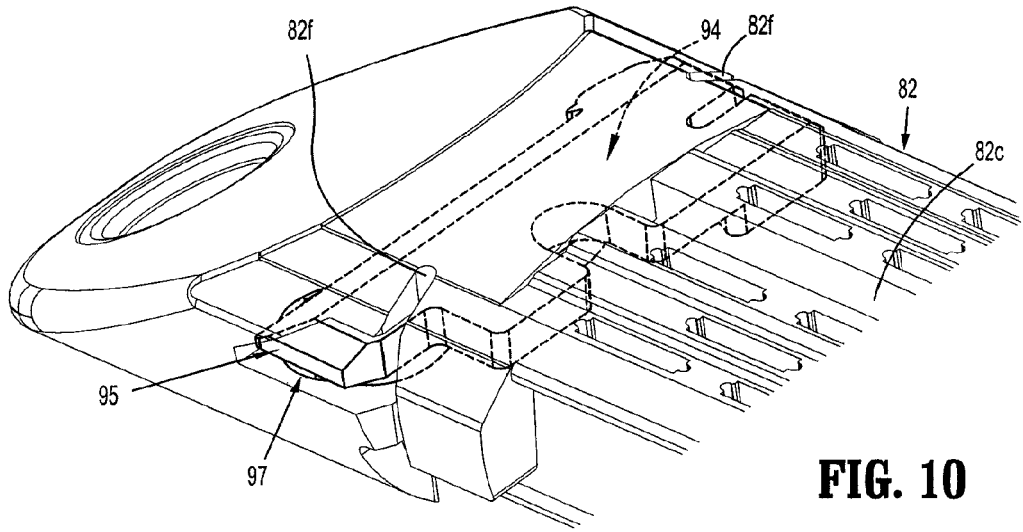
FIG. 10 is a top, perspective view of a distal end of a cartridge assembly of the DLU including a suture release assembly according to an embodiment of the present disclosure.

As seen in FIGS. 8 and 9, suture release assembly 74 includes an open or release configuration wherein finger 76c of anchor bar 76 does not extend into or overlie the respective one of the pair of distal recesses 70e in operative registration therewith, release bar 77c of actuation member 77 does not extend across knife slot 70b of anvil plate 70, and pin 77d of release bar 77c is disposed at or near a second end of arcuate slot 75a of guide plate 75.

Suture release assembly 74 is used by a manufacturer during the assembly process of surgical stapling apparatus 10 to secure, with a surgical suture or tether, a surgical anvil buttress "B" to a tissue contacting surface of the anvil plate 70, and by the end user of surgical stapling apparatus 10 to automatically release or free the surgical anvil buttress "B" from the tissue contacting surface of the anvil plate 70 upon a complete firing of the surgical stapling apparatus 10.

With reference to FIGS. 6-9, during the manufacturing process, with suture release assembly 74 in the open or release configuration (FIGS. 8 and 9), a surgical anvil buttress "B" is laid over the tissue contacting surface of anvil plate 70. Then, a first end of a surgical suture "S1" is inserted into one of the pair of distal recesses 70e and a second end of surgical suture "S1" is extended across the surgical anvil buttress "B1" (see FIG. 2) and inserted into the other of the pair of distal recesses 70e. It is contemplated that the first end of surgical suture "S1" may include a knot, stop or the like (not shown) sized so as to not pass through the narrower recess of the distal pair of recesses 70e.

With the second end of the surgical suture "S1" disposed in the pair of distal recesses 70e, and with the surgical suture "S1" pulled taught across the surgical anvil buttress "B", a tool (not shown) is inserted through arcuate slot 75a of guide plate 75 and engaged with an opening provided in the pin 77d of release bar 77c. With reference to FIGS. 6 and 7, the tool is then manipulated to move through or along arcuate slot 75a of guide plate 75, thereby actuating or moving release bar 77c and rotating eccentric cam 77a. As eccentric cam 77a is rotated, boss 77b is rotated around the pivot axis of eccentric cam 77a and acts on the walls of elongate slot 76b of anchor bar 76 thereby causing anchor bar 76 to pivot. As anchor bar 76 is pivoted, finger 76c thereof is caused to extend into or overlies one of the distal recesses 70e and to pinch the second end of the surgical suture disposed therewithin. Meanwhile, release bar 77c has been moved to a position extending across knife slot 70b of anvil plate 70. Suture release assembly 74 is now in the locking or anchoring configuration, as described above. The distal recess 70e that cooperates with the finger 76c is desirably relatively wide so as to allow the suture "S1" to easily pass into and out of the recess 70e when the 76 anchor bar is away from the recess 70e. The other distal recess 70e, arranged on the opposite lateral side of the anvil plate 70, may be the same size, or may be small enough to cinch the suture "S1" and hold the suture in place to facilitate assembly.

In operation, with surgical anvil buttress "B1" secured against the lower surface of anvil plate 70, during firing of surgical stapling apparatus 10, as drive assembly 50 is advanced (i.e., moved from a proximal-most position to a distal-most position), knife blade 66 slices through a central section of the proximal suture "S2", thereby freeing the proximal end of the surgical anvil buttress "B1" from anvil assembly 20. During use, as the firing stroke of surgical stapling apparatus 10 is nearing completion and as drive assembly 50 approaches a distal end of knife slot 70b of anvil plate 70, as seen in FIG. 9, drive assembly 50 contacts release bar 77c, urging release bar 77c and, in turn, eccentric cam 77a to rotate about the pivot axis thereof. As eccentric cam 77a is rotated, boss 77b is rotated around the pivot axis of eccentric cam 77a and acts on the walls of elongate slot 76b of anchor bar 76 thereby causing anchor bar 76 to pivot. As anchor bar 76 is pivoted, finger 76c thereof is caused to move away from the relatively wider distal recess 70e and to release the second end of the surgical suture "S" disposed therewithin. With the second end of surgical suture "S" released or free, the distal end of the surgical anvil buttress "B1" is free to separate from the tissue contacting surface of anvil plate 70.

As seen in FIGS. 1 and 2, cartridge assembly 18 includes a carrier 80 defining an elongated support channel 80a. Elongated support channel 80a of carrier 80 receives a staple cartridge 82 therein. Corresponding tabs and slots formed along staple cartridge 82 and carrier 80 function to retain staple cartridge 82 within carrier 80. A pair of support struts formed on and extending from staple cartridge 82 are positioned to rest on side walls of carrier 80 to further stabilize staple cartridge 82 within support channel 80a of carrier 80. Staple cartridge 82 includes retention slots 82a formed therein for receiving a plurality of fasteners 84 and pushers 86. A plurality of spaced apart longitudinal slots 82b extend through staple cartridge 82 to accommodate upstanding cam wedges 90a of an actuation sled 90. The actuation sled 90 includes a central upstanding wedge or wall 90b. Central wall 90b defines a distal notch or shoulder 90c formed therein (See FIG. 2).

A central longitudinal slot 82c is formed in and extends along the length of staple cartridge 82 to facilitate passage of central wall portion 62 of head 60 therethrough. During operation of surgical stapler 10, actuation sled 90 translates through longitudinal slots 82b of staple cartridge 82 to advance cam wedges 90a into sequential contact with pushers 92, to cause pushers 92 to translate vertically within retention slots 82a and urge fasteners 84 (e.g., staples) from slots 82a into the staple forming cavities 70a of anvil plate 70 of anvil assembly 20.

With continued reference to FIGS. 1 and 2, staple cartridge 82 defines a proximal pair of recesses 82e formed near a proximal end thereof and disposed, one each, on opposed sides of longitudinal slot 82c. Staple cartridge 82 further defines a distal pair of recesses 82f formed near a distal end thereof and disposed, one each, on opposed sides of longitudinal slot 82c. In one embodiment, at least one of the recesses of each of the proximal pair of recesses 82e and the distal pair of recesses 82f is preferably non-circular and constricting or otherwise arranged so as to frictionally engage and/or pinch an anchor "S".

Figure 2B:
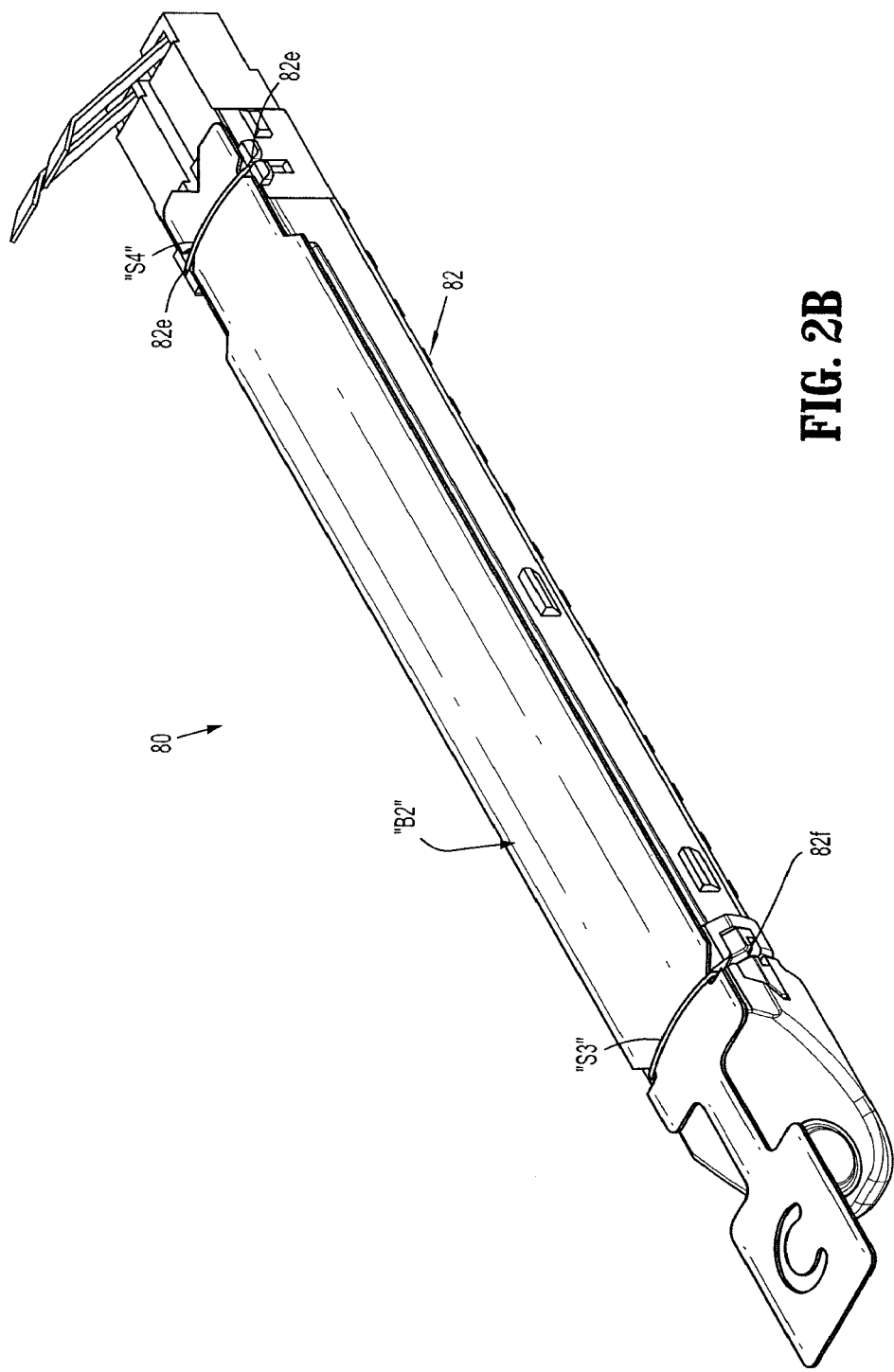
FIG. 2B is an enlarged perspective view of a cartridge assembly of the loading unit illustrating a surgical cartridge buttress secured to a tissue contacting surface thereof.
Figure 3:
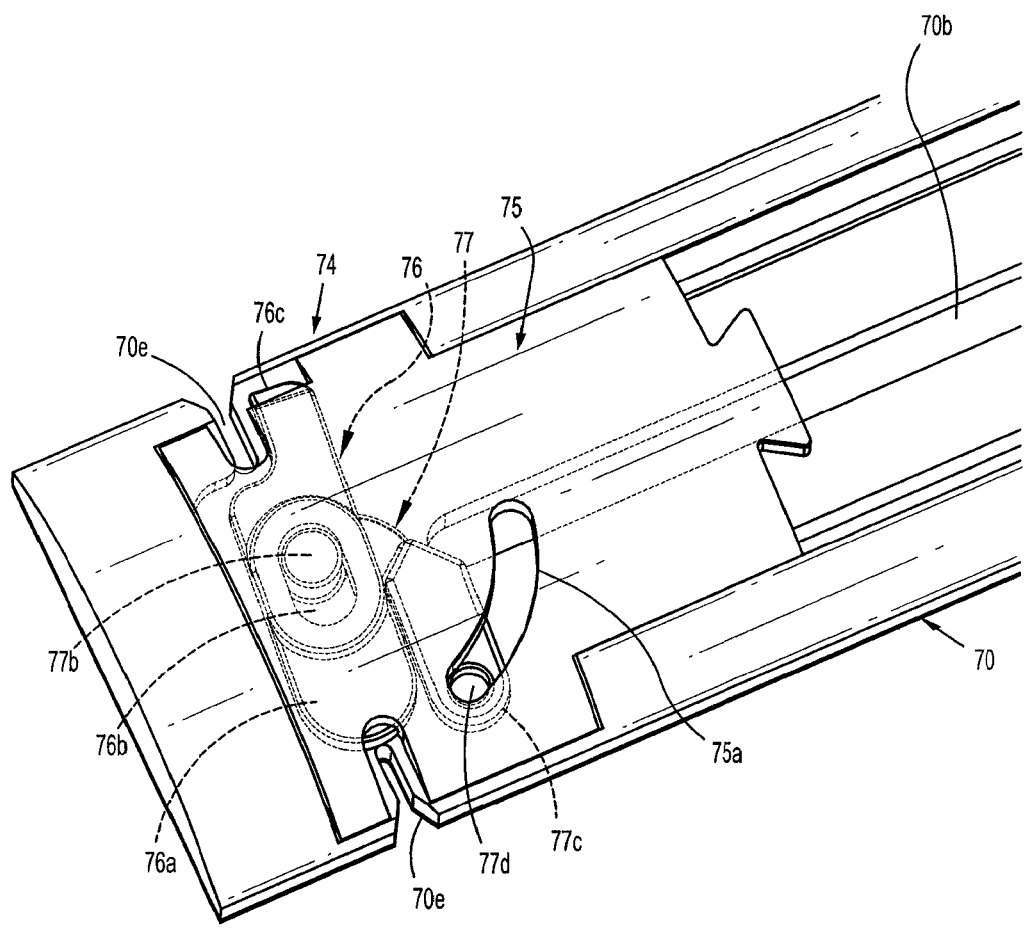
FIG. 3 is a top, perspective view of a distal end of an anvil assembly of the loading unit including a suture release assembly according to an embodiment of the present disclosure, shown in an open configuration.

As seen in FIGS. 1 and 2B, cartridge assembly 18 further includes a surgical cartridge buttress "B2", pledget or the like operatively secured to an upper surface or tissue contacting surface of staple cartridge 82, by anchors "S3" and "S4", to overlie at least some of staple pockets 82a and/or at least a portion of a length of longitudinal slot 82c. In particular, an anchor "S4" is wrapped around a proximal portion of surgical cartridge buttress "B2" and cinched in each of the proximal pair of recesses 82e and an anchor "S3" is wrapped around a distal portion of the surgical cartridge buttress "B2" and cinched in each of the distal pair of recesses 82f.

In one particular embodiment, a first end of each anchor "S" includes a knot, stop or the like (not shown) sized so as to not pass through one recess of the proximal pair of recesses 82e and a second end of each anchor "S" passes over, and transversely across, surgical cartridge buttress "B2", at least once, and back through the other recess of the proximal pair of recesses 82e. For example, the second end of each anchor "S" may be pinched or cinched in the other recess of the proximal pair of recesses 82e so as to anchor the second end of the anchor "S" and secure the surgical cartridge buttress "B2" against the tissue contacting surface of staple cartridge 82. Similarly, an anchor "S3" is used to extend transversely across surgical cartridge buttress "B2" and into engagement with the distal pair of recesses 82f.

In a further embodiment, the release assembly is arranged to cut the suture "S." The arcuate slot 75a on the guide plate 75 extends in the opposite direction so that it is arranged to drive the anchor bar 95 toward the suture "S." The surface of the anchor bar 76 that faces the suture S includes a sharpened edge and cuts the suture when actuated by the drive assembly.

Surgical cartridge buttress "B2" includes a proximal pair of notches formed in side edges aligned with the proximal pair of recesses 82e of staple cartridge 82, a distal pair of notches formed in side edges thereof aligned with the distal pair of recesses 82f of staple cartridge 82, and a proximal notch formed in a proximal edge thereof aligned with longitudinal slot 82c when surgical cartridge buttress "B2" is secured to staple cartridge 82. Surgical cartridge buttress "B2" further includes a tongue or tab extending from a distal edge thereof to facilitate with the attachment of surgical cartridge buttress "B2" to staple cartridge 82 during the assembly process. It is contemplated that a width of surgical cartridge buttress "B2" may be reduced in a proximal portion thereof. It is further contemplated that the tongue is removed from surgical cartridge buttress "B2" following securement of surgical cartridge buttress "B2" to staple cartridge 82 and prior to packaging or shipment.

As seen in FIGS. 2 and 10-14, cartridge assembly 18 further includes a cartridge release assembly 94 supported in and near a distal end of staple cartridge 82. Release assembly 94 includes a lock or anchor bar 95 pivotally connected to staple cartridge 82. Anchor bar 95 includes a body portion 95a having a finger 95b extending from an edge thereof. Finger 95b is in operative registration with one of the distal pair of recesses 82f, preferably, the one of the distal pair of recesses having the relatively larger width dimension.

Figure 11:
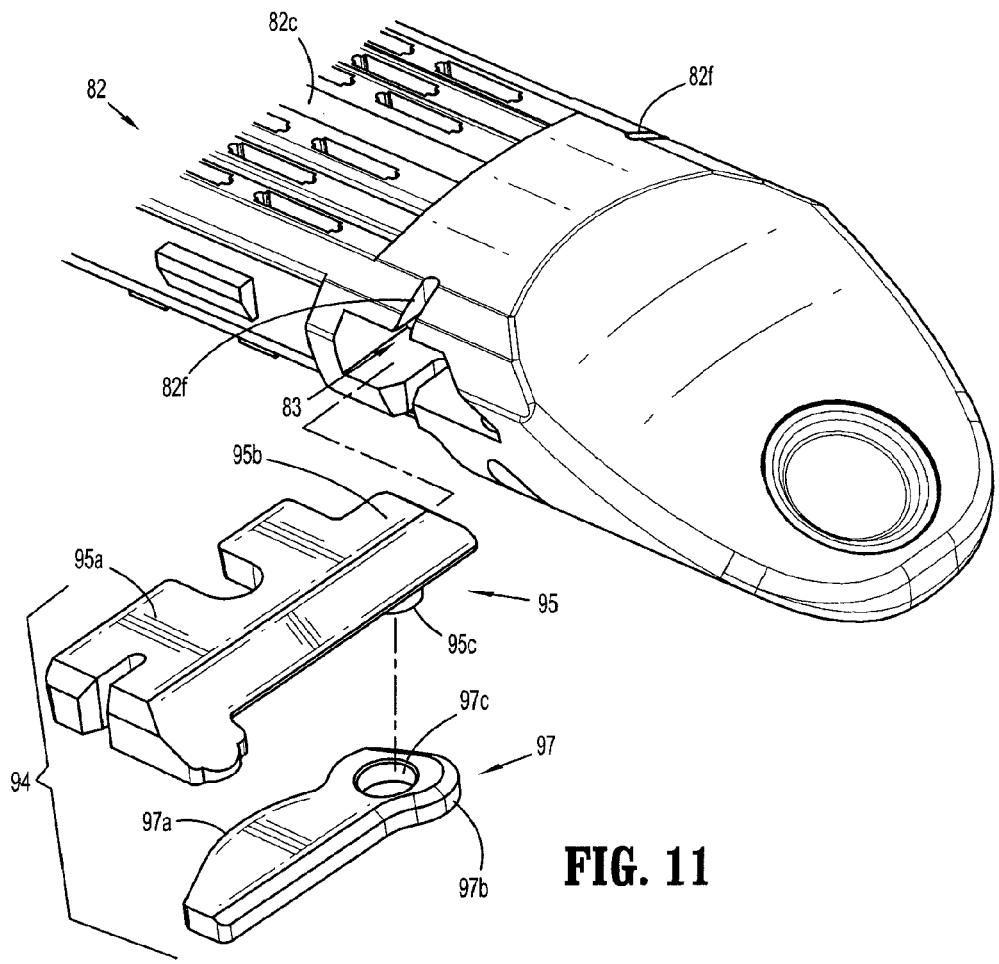
FIG. 11 is a top, perspective view of the cartridge assembly of FIG. 10, illustrating the parts of the suture release assembly thereof separated.
Figure 12:
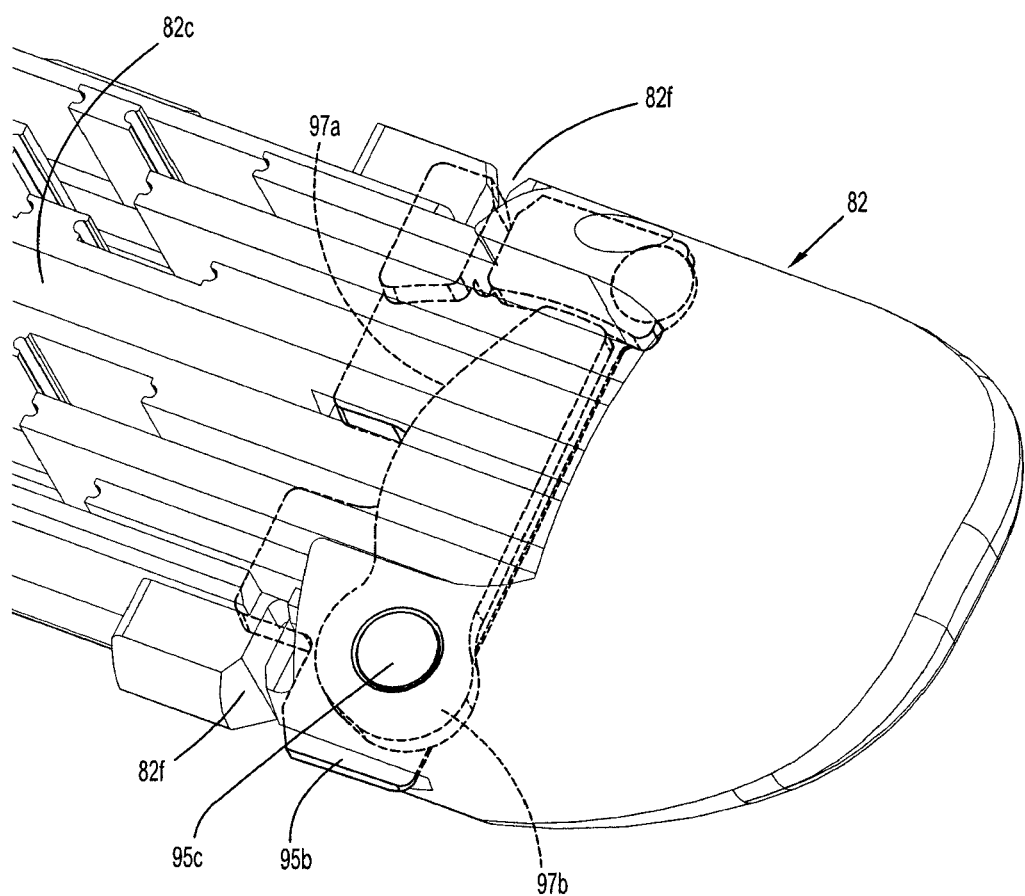
FIG. 12 is a bottom, perspective view of a distal end of the cartridge assembly of FIGS. 10 and 11.

Release assembly 94 further includes an anchor bar actuation member 97 pivotally connected to anchor bar 95 (as seen in FIGS. 11 and 12). Actuation member 97 includes a first cam surface 97a located along a proximal edge of actuation member 97 and extending across central longitudinal slot 82c of staple cartridge 82, and a second eccentric cam surface 97b extending distally and laterally from actuation member 97 in close proximity to the one of the distal pair of recesses 82f that is operatively associated with finger 95b of anchor bar 95. First cam surface 97a of actuation member 97 is substantially arcuate or convex. Actuation member 97 defines an aperture or opening 97c configured and dimensioned to receive a pin 95c of anchor bar 95 therein so as to anchor bar 95 and actuation member 97 to pivot or rotate relative to one another.

In operation, rotation of actuation member 97 in a first direction, about its pivot point, results in second cam surface 97b pressing against a surface 82g (see FIGS. 13 and 14) of staple cartridge 82 and thus moving finger 95b at least partially over and/or across the one of the distal pair of recesses 82f associated therewith.

Figure 13:
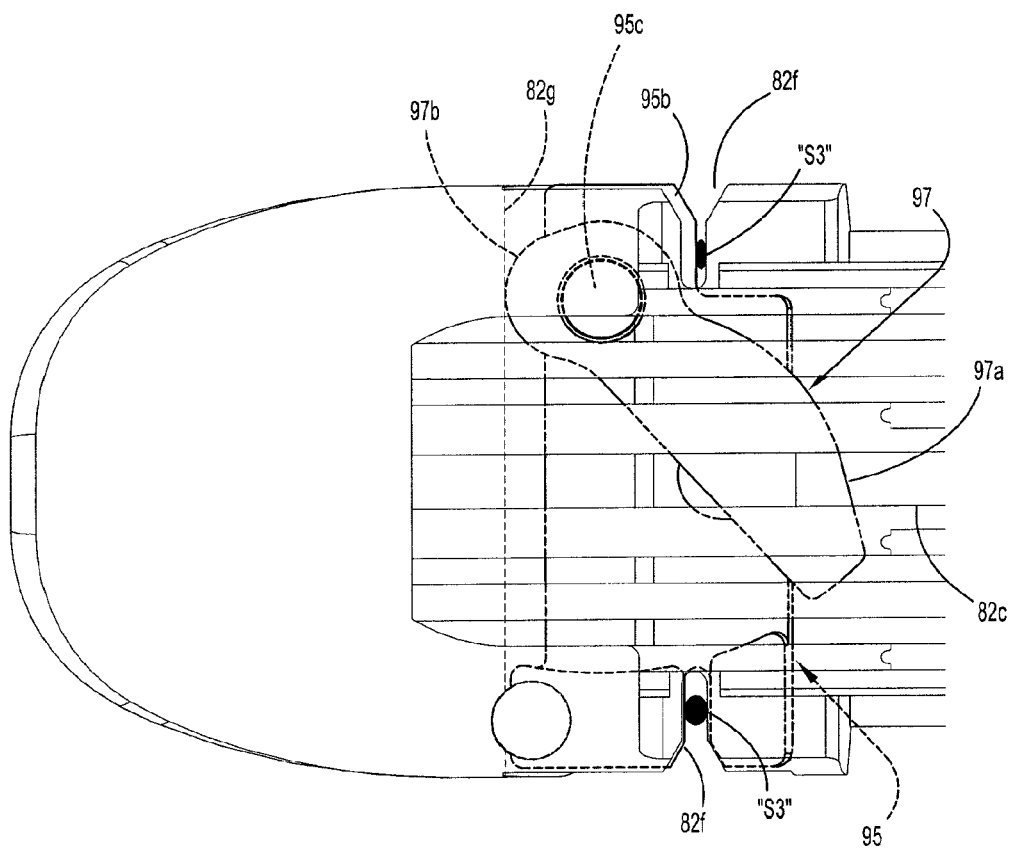
FIG. 13 is a top, plan view of the cartridge assembly of FIGS. 10-12, illustrating the suture release assembly thereof in the closed configuration.

As seen in FIG. 13, suture release assembly 94 includes a locking or anchoring configuration wherein first cam surface 97a of actuation member 97 extends into and across central longitudinal slot 82c of staple cartridge 82, wherein second cam surface 97b of actuation member 97 is pressed against surface 82g of staple cartridge 82, and thus finger 95b of anchor bar 95 extends into or overlies the respective one of the pair of distal recesses 82f in operative registration therewith. Fastener release assembly 94 may be maintained in the locking or anchoring configuration by way of a biasing member or a detent that engages actuation member 97 in a manner so as to keep actuation member 97 in the locked or anchoring configuration. When in such a locked or anchoring configuration, the suture "S3" may be urged into recess 82f of staple cartridge 82. It is contemplated that suture release assembly 94 may include a friction fit or snap fit feature for maintaining and/or retaining suture release assembly 94 in the locking or anchoring configuration at all times following the manufacturing/assembly process and prior to a complete firing of surgical stapling apparatus 10.

Figure 14:
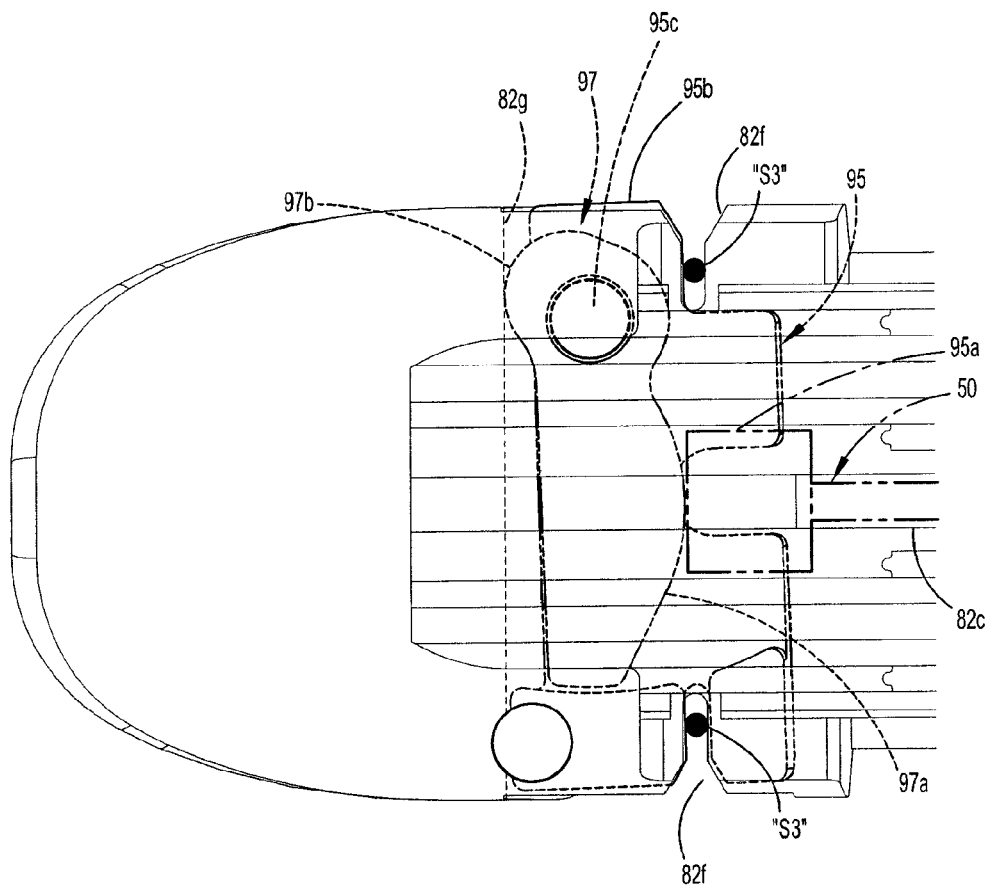
FIG. 14 is a top, plan view of the cartridge assembly of FIGS. 10-13, illustrating the suture release assembly thereof in the open configuration.
Figure 17:
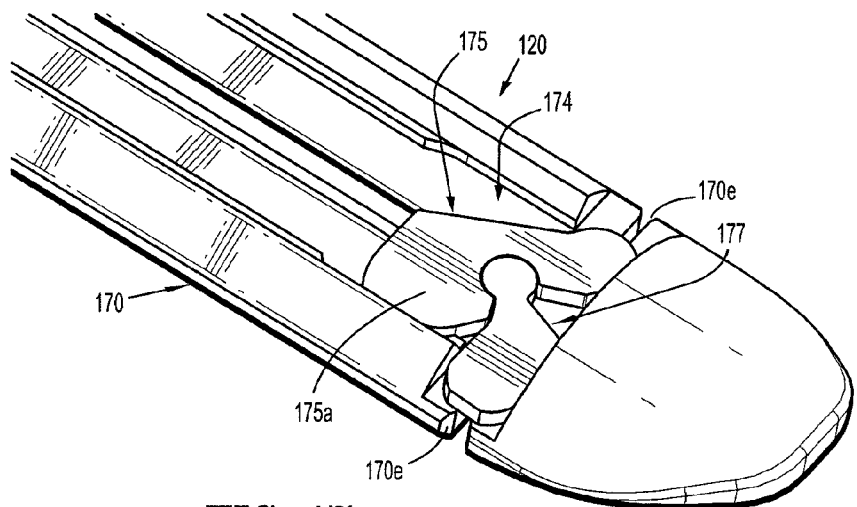
FIG. 17 is a top, perspective view of a distal end of an anvil assembly (with an anvil cover removed), illustrating a suture release assembly thereof in an actuated configuration.

As seen in FIGS. 12 and 14, suture release assembly 94 includes an open or release configuration wherein finger 95b of anchor bar 95 does not extend into or overlie the respective one of the pair of distal recesses 82f in operative registration therewith, first cam surface 97a of actuation member 97 does not extend into and across central longitudinal slot 82c of staple cartridge 82, and second cam surface 97b of actuation member 97 is not pressed against surface 82g of staple cartridge 82.

Suture release assembly 94 is used by a manufacturer during the assembly process of surgical stapling apparatus 10 to secure, with an anchor, surgical suture, or tether "S", a surgical cartridge buttress "B2" (see FIG. 2) to a tissue contacting surface of the staple cartridge 82, and by the end user of surgical stapling apparatus 10 to automatically release or free the surgical cartridge buttress "B2" from the tissue contacting surface of the staple cartridge 82 upon a complete firing of the surgical stapling apparatus 10.

With reference to FIGS. 10-14, during the manufacturing process, with suture release assembly 94 in the open or release configuration, a surgical cartridge buttress "B2" is laid over the tissue contacting surface of staple cartridge 82. Then, a first end of a surgical suture "S" is inserted into the relatively narrower of the pair of distal recesses 82f and a second end of surgical suture "S" is extended across the surgical cartridge buttress "B2" and inserted into the relatively wider of the pair of distal recesses 82f. It is contemplated that the first end of surgical suture "S" may include a knot, stop or the like (not shown) sized so as to not pass through the narrower recess of the distal pair of recesses 82f.

As seen in FIG. 11, staple cartridge 82 includes an access opening 83 formed therein which is used to insert and receive suture release assembly 94 therein and to provide access to actuation member 97. With the second end of the surgical suture "S" disposed in the relatively wider of the pair of distal recesses 82f, and with the surgical suture "S" pulled taught across the surgical cartridge buttress "B2," actuation member 97 is rotated about the pivot axis causing first cam surface 97a of actuation member 97 to extend into and across central longitudinal slot 82c of staple cartridge 82 and causing second cam surface 97b of actuation member 97 to press against surface 82g (see FIGS. 13 and 14) of staple cartridge 82. In so doing, anchor bar 95 is pivoted by an amount sufficient for finger 95b of anchor bar 95 to extend into or overlies the respective one of the pair of distal recesses 82f in operative registration therewith thereby pinch the second end of the surgical suture disposed therewithin. Suture release assembly 94 is now in the locking or anchoring configuration, as described above.

In operation, with surgical cartridge buttress "B1" secured against the tissue contacting surface of staple cartridge 82, during firing of surgical stapling apparatus 10, as drive assembly 50 is advanced (i.e., moved from a proximal-most position to a distal-most position), knife blade 66 slices through a central section of the proximal suture "S4", thereby freeing the proximal end of the surgical cartridge buttress "B2" from staple cartridge 82. During use, as the firing stroke of surgical stapling apparatus 10 is nearing completion and as drive assembly 50 approaches a distal end of central longitudinal slot 82c of staple cartridge 82, as seen in FIG. 14, drive assembly 50 contacts first cam surface 97a of actuation member 97, urging actuation member 97 to rotate. Second cam surface 97b of actuation member 97 also rotates about the pivot axis of pivot pin 95c thereof. As eccentric second cam surface 97b is rotated about the pivot axis second cam surface 97b, the distance between the pivot pin 95c and the surface 82g of staple cartridge 82 is reduced thereby pivoting anchor bar 95 about pivot pin 95c. As anchor bar 95 is pivoted, finger 95c thereof is caused to move away from the relatively wider distal recess 82f and to release the second end of the surgical suture "S" disposed therewithin. With the second end of surgical suture "S" released or free, the distal end of the surgical cartridge buttress "B2" is free to separate from the tissue contacting surface of staple cartridge 82. The distal recesses 82f that is in operative registration with finger 95b of anchor bar 95 is dimensioned so that, notwithstanding the rotation of anchor bar 95, the suture "S3" is not cinched therewithin.

As drive assembly 50 is advanced from the proximal position to the distal position, knife blade 66 thereof slices or cuts longitudinally through both surgical anvil buttress "B1" and surgical cartridge buttress "B2", thereby dividing the buttresses "B1, B2" substantially in half. Additionally, as drive assembly 50 is advanced from a proximal-most position to a distal-most position, upstanding cam wedges 90a of actuation sled 90 actuates pushers 92, to cause pushers 92 to translate vertically within retention slots 82a and urge fasteners 84 from slots 82a. As fasteners 84 (e.g., staples) are urged from slots 82a of staple cartridge 82, legs of fasteners 84 penetrate and pass through both surgical anvil buttress "B1" and surgical cartridge buttress "B2", through any tissue (not shown) interposed between surgical anvil buttress "B1" and surgical cartridge buttress "B2", and are formed against or within staple forming cavities 70a of anvil plate 70 of anvil assembly 20. Buttresses "B1, B2" preferably include perforations that divide the buttresses and facilitate removal of the apparatus from the tissue.

According to the present disclosure, surgical anvil buttress "B1" and/or surgical cartridge buttress "B2" is pre-loaded (i.e., from the manufacturer) onto anvil assembly 20 or cartridge assembly 18, respectively, of the loading unit 16. After the loading unit is fired, an additional unfired loading unit, with or without buttresses "B", can be loaded onto the surgical apparatus. In certain embodiments, the replaceable loading unit is a removable cartridge that can be inserted into support channel of carrier 80. A buttress and release assembly may be pre-loaded onto the removable cartridge and means for the user of the surgical apparatus to load a buttress onto the anvil assembly can be provided. For example, a buttress having an adhesive can be used. Additional or replacement buttresses "B" for anvil assembly 20 and/or cartridge assembly 18 may be secured to either anvil assembly 20 or cartridge assembly 18 as needed or desired.

In a further embodiment, the release assembly may be arranged to cut the suture "S." The cam surface 97b on the actuation member 97 may be arranged to cam the anchor bar 95 toward the suture "S." The surface of the anchor bar 97 that faces the suture "S" may include a sharpened edge and may cut the suture when actuated by the drive assembly.

Turning now to FIGS. 15-25, a loading unit according to another embodiment of the present disclosure, for surgical stapling apparatus 10, is generally designated as 116. Loading unit 116 is substantially similar to loading unit 16 and will only be discussed in detail herein to the extent necessary to identify differences in construction and operation.

Figure 18:
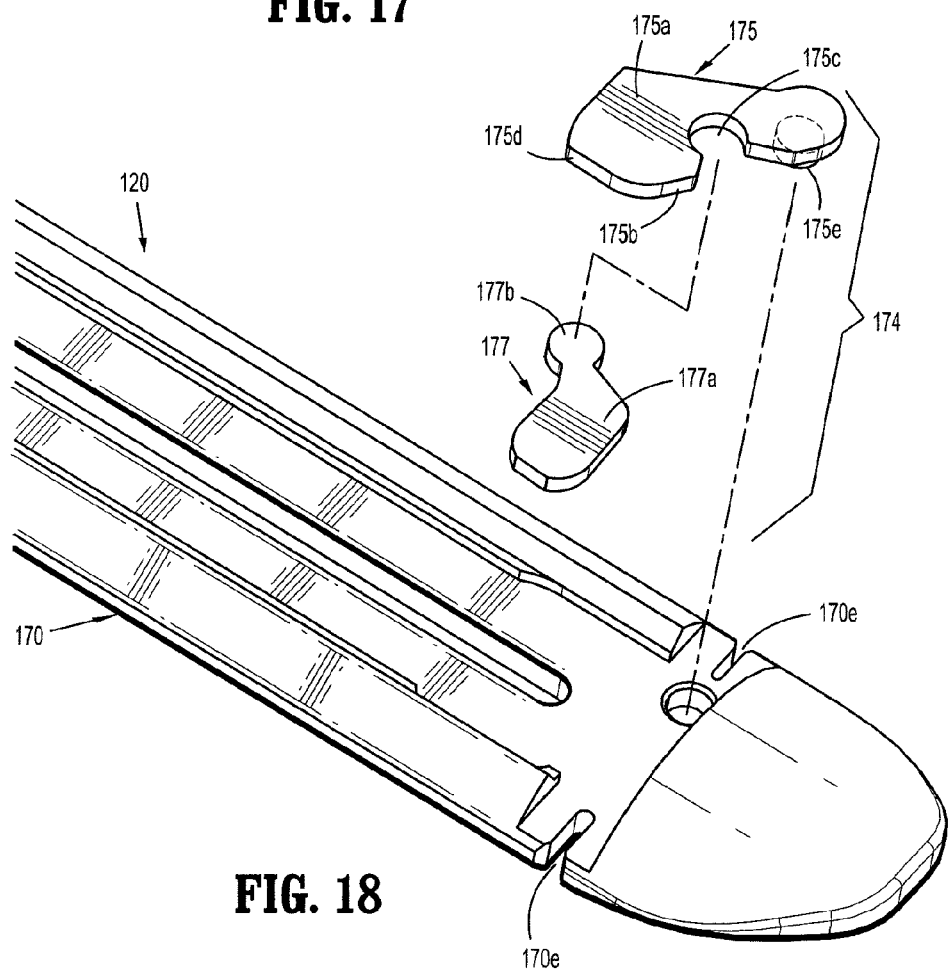
FIG. 18 is a top, perspective view of the distal end of the anvil assembly of FIG. 17, illustrating the parts of the suture release assembly thereof separated.
Figure 19:
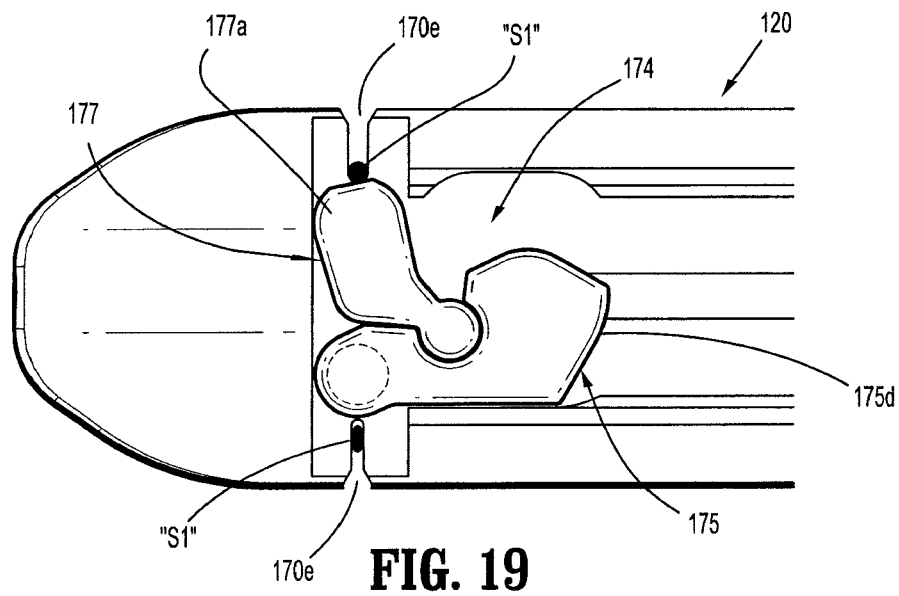
FIG. 19 is a top, plan view of the anvil assembly of FIGS. 17 and 18, illustrating the suture release assembly thereof in an unactuated configuration.
Figure 20:
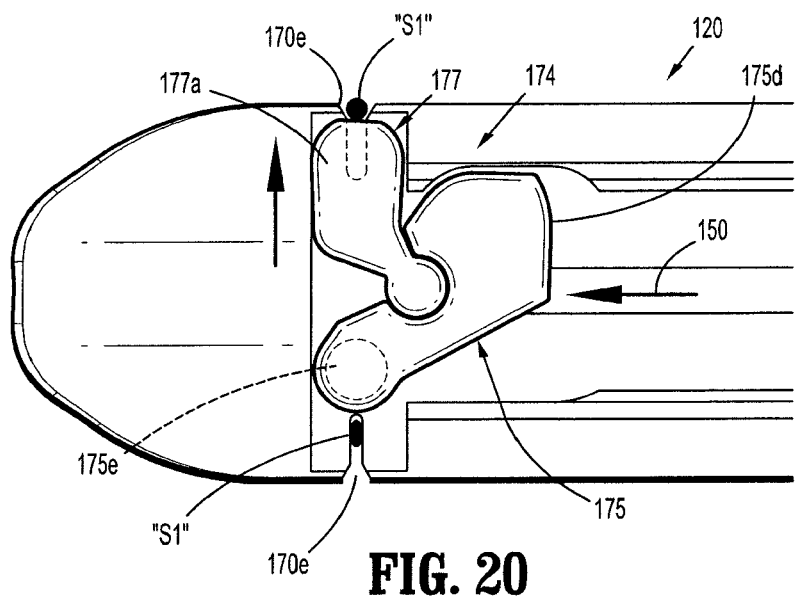
FIG. 20 is a top, plan view of the anvil assembly of FIGS. 17-19, illustrating the suture release assembly thereof in an actuated configuration.
Figure 21:
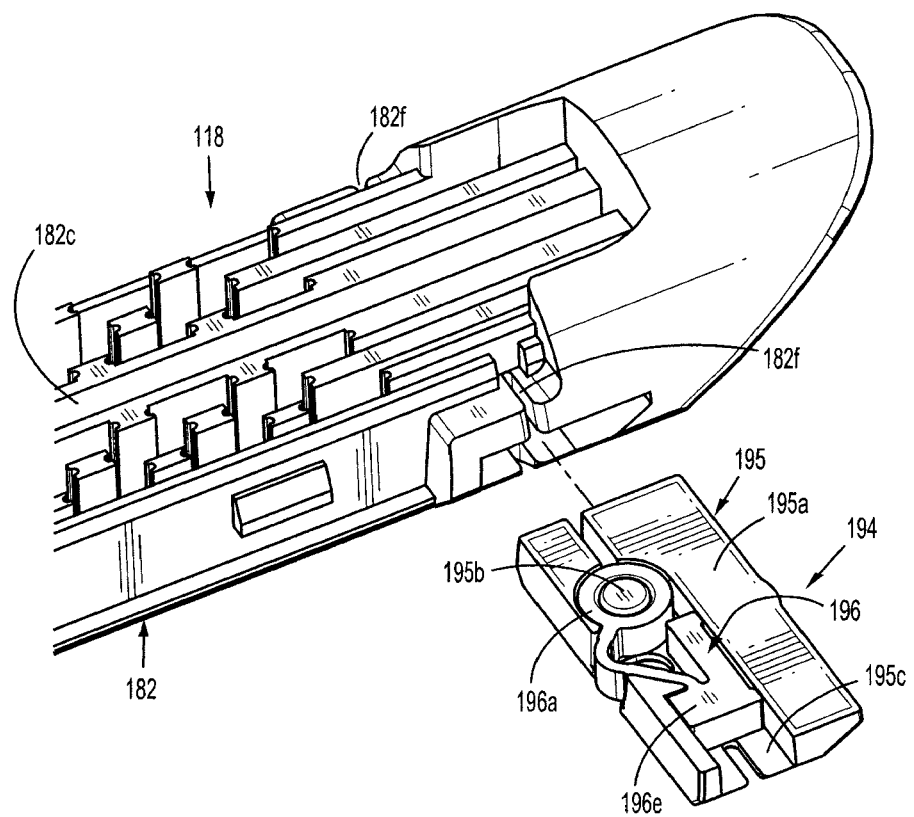
FIG. 21 is a bottom, perspective view of a distal end of a cartridge assembly of the DLU of FIG. 15, illustrating a suture release assembly thereof separated therefrom.
Figure 22:
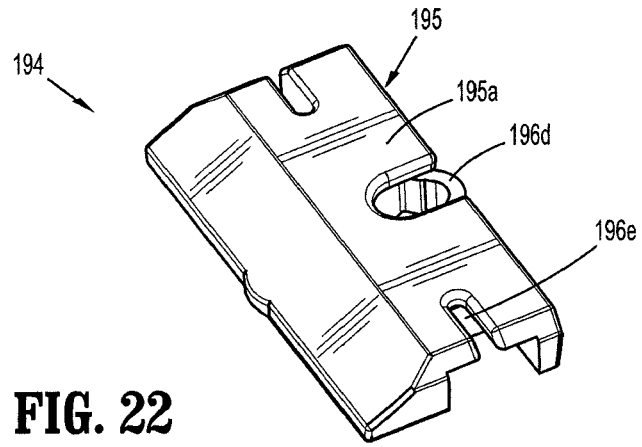
FIG. 22 is a top, perspective view of the suture release assembly of FIG. 21.
Figure 23:
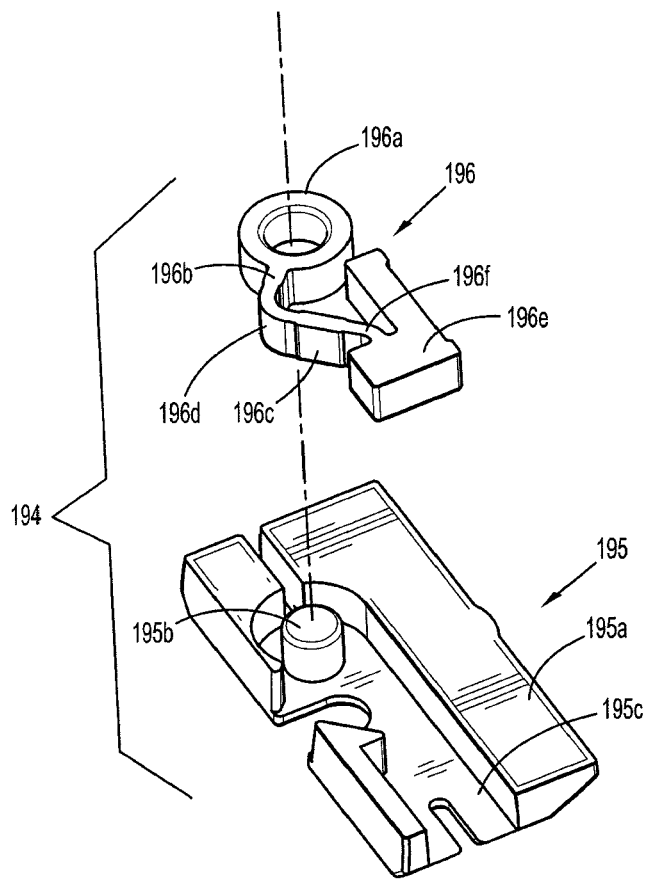
FIG. 23 is a bottom, perspective view, with parts separated, of the suture release assembly of FIGS. 21 and 22.

As seen in FIGS. 15-20, anvil assembly 120 of loading unit 116 includes a suture release assembly 174 disposed between anvil plate 170 and cover plate 172 at a location in operative registration with the distal pair of recesses 170e. Suture release assembly 174 includes a link arm 175 pivotally connected to anvil plate 170 (as seen in FIG. 18) and/or optionally cover plate 172. Link arm 175 includes a body portion 175a defining a pocket or recess 175c formed in a first side edge 175b thereof and a camming surface 175d defined substantially along an adjacent side or proximal edge thereof. Pocket 175c has a substantially arcuate, circular or rounded profile. As seen in FIGS. 18 and 20, link arm 175 includes a pivot pin 175e extending from body portion 175a for pivotally connecting link arm 175 to anvil assembly 120.

Release assembly 174 further includes a pusher bar 177 pivotally connected to link arm 175 and slidably disposed between anvil plate 170 and cover plate 172. Pusher bar 177 includes a body portion 177a having a substantially rectangular configuration and a head 177b, extending from a corner of body portion 177a, and having a substantially circular or rounded configuration. Head 177b of pusher bar 177 is configured and dimensioned for pivotable and/or rotatable connection in pocket 175c of link arm 175.

As seen in FIG. 19, suture release assembly 174 includes an unactuated configuration wherein pusher bar 177 does not extend into or overlie the respective one of the pair of distal recesses 170e in operative registration therewith, and a longitudinal axis of link arm 175 is oriented substantially parallel with a longitudinal axis of loading unit 116. It is contemplated that suture release assembly 174 may include a friction fit or snap fit feature for maintaining and/or retaining suture release assembly 174 in the locking or anchoring configuration at all times following the manufacturing/assembly process and prior to a complete firing of the surgical stapling apparatus.

As seen in FIG. 20, suture release assembly 174 includes an actuated configuration wherein pusher bar 177 extends into or overlies the respective one of the pair of distal recesses 170e in operative registration therewith, and a longitudinal axis of link arm 175 is oriented substantially transverse to the longitudinal axis of loading unit 116.

With reference to FIGS. 15-20, during the manufacturing process, with suture release assembly 174 in the unactuated configuration, a surgical anvil buttress (not shown) is laid over the tissue contacting surface of anvil plate 170. Then, a first end of a surgical suture "S1" is inserted into one of the pair of distal recesses 170e and a second end of surgical suture "S1" is extended across the surgical anvil buttress (not shown) and inserted into the other of the pair of distal recesses 170e. It is contemplated that each of the pair of distal recesses 170e is an open ended constricting slot so as to frictionally grip or cinch a surgical suture "S1" disposed therein.

In operation, with a surgical anvil buttress (not shown) secured against the lower surface of anvil plate 170, during firing of the surgical stapling apparatus, as drive assembly 150 is advanced (i.e., moved from a proximal-most position to a distal-most position), knife blade 166 slices through a central section of the proximal suture (not shown), thereby freeing the proximal end of the surgical anvil buttress (not shown) from anvil assembly 120. During use, as the firing stroke of the surgical stapling apparatus is nearing completion and as drive assembly 150 approaches a distal-most end of knife slot 170b of anvil plate 170, as seen in FIG. 20, drive assembly 150 contacts camming surface 175d of link arm 175, thus urging link arm 175 to rotate or pivot around the pivot pin and, in turn, urging pusher bar 177 to translate in the direction of the slot. As pusher bar 177 is translated, pusher bar 177 comes into contact with and urges the second end of suture "S1" out of the distal recess 170e that is registration therewith to release the second end of suture "S1" therefrom. With the second end of surgical suture "S1" released or free from distal recess 170e, the distal end of the surgical anvil buttress "B1" is free to separate from the tissue contacting surface of anvil plate 170.

As seen in FIGS. 15, 16 and 21-25, cartridge assembly 118 of loading unit 116 includes a cartridge release assembly 194 supported in and near a distal end of staple cartridge 182. Release assembly 194 includes a retainer 195 supported in a distal end of staple cartridge 182 at a location near a distal end of longitudinal slot 182c and at least partially extending thereacross. Retainer 195 includes a body portion 195a, a boss 195b extending from a surface thereof, and defines a channel or recess 195c formed in a surface thereof and extending through a side thereof. When supported in staple cartridge 182, recess 195c of retainer 195 is in registration with one of the pair of distal recesses 182f of staple cartridge 182.

Release assembly 194 further includes a pusher member 196 having a head portion 196a pivotally connected to boss 195b of retainer 195. Pusher member 196 further includes a first leg member 196b extending from head portion 196a and a second leg member 196c connected to a free end of first leg member 196b via a living hinge connection 196d. Pusher member 196 further includes piston 196e connected to a free end of second leg member 196c via a living hinge connection 196f. Piston 196e is slidably disposed and translatable within recess 195c of retainer 195. In certain other embodiments, the pusher is a linkage assembly having a first link pivotally connected to the cartridge at one end. The other end of the first link is pivotally connected to a first end of a second link. The opposite, second, end of the second link is confined in the recess of the retainer.

Figure 24:
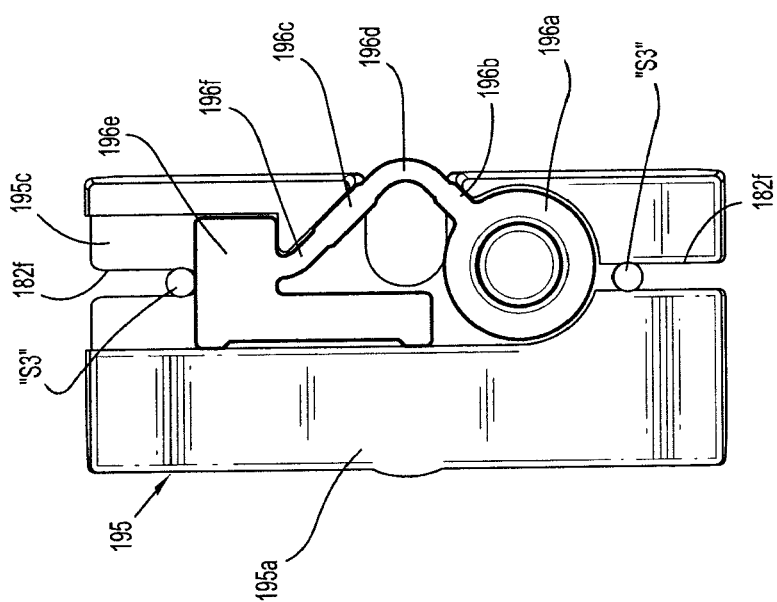
FIG. 24 is a top, plan view of the suture release assembly of FIGS. 21-23, illustrating the suture release assembly thereof in an unactuated configuration.
Figure 26:
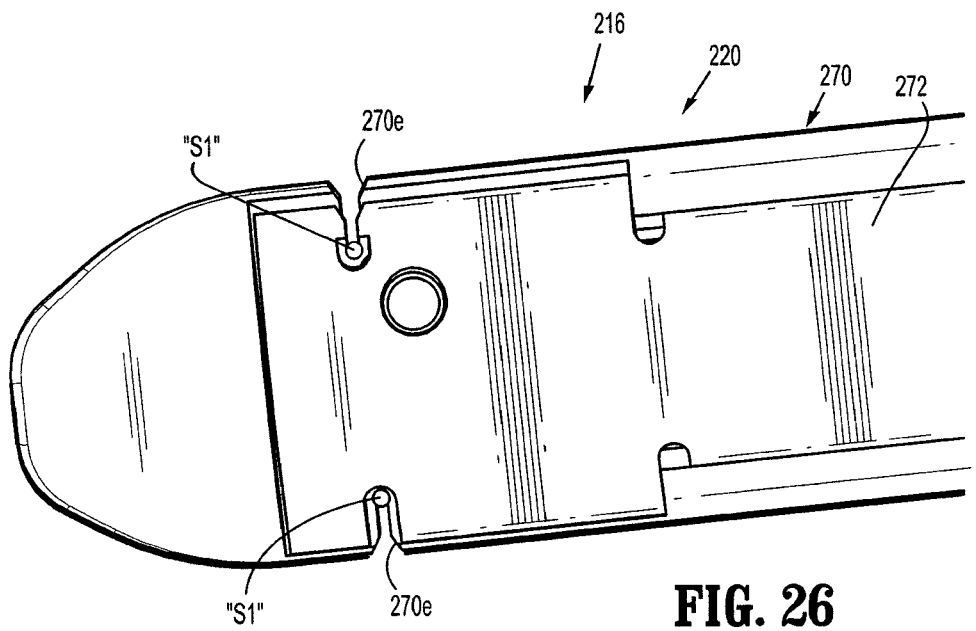
FIG. 26 is a top, plan view of a distal end of an anvil assembly of a loading unit including a suture release assembly according to yet another embodiment of the present disclosure.

As seen in FIG. 24, release assembly 194 includes an unactuated configuration wherein piston 196e does not extend into or overlie the respective one of the pair of distal recesses 182f, and first leg member 196b and second leg member 196c are angled with respect to one another and project proximally along longitudinal slot 182c of staple cartridge 182. It is contemplated that suture release assembly 194 may include a friction fit or snap fit feature for maintaining and/or retaining suture release assembly 194 in the locking or anchoring configuration at all times following the manufacturing/assembly process and prior to a complete firing of the surgical stapling apparatus.

Figure 25:
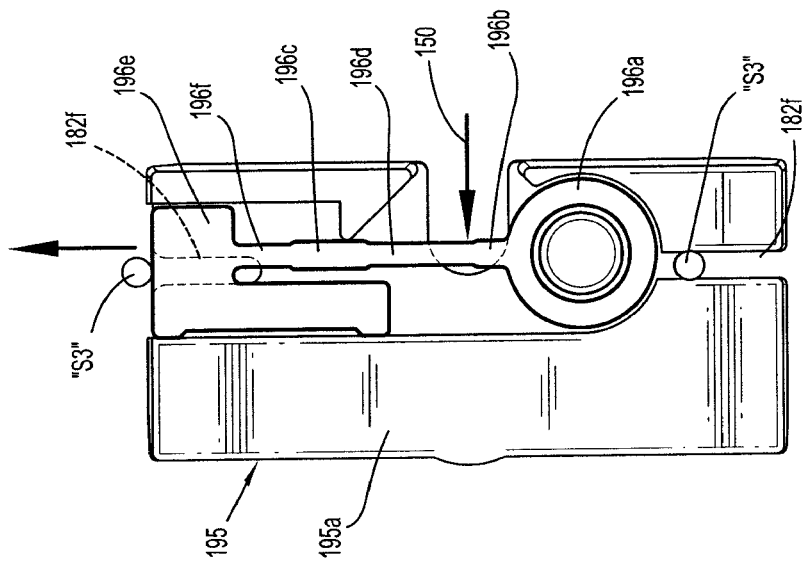
FIG. 25 is a top, plan view of the suture release assembly of FIGS. 21-24, illustrating the suture release assembly thereof in an actuated configuration.

As seen in FIG. 25, suture release assembly 194 includes an actuated configuration wherein piston 196e extends into or overlies the respective one of the pair of distal recesses 182f in operative registration therewith, and first leg member 196b and second leg member 196c are extended substantially along a common axis.

With reference to FIGS. 21-25, during the manufacturing process, with suture release assembly 194 in the unactuated configuration, a surgical cartridge buttress (not shown) is laid over the tissue contacting surface of staple cartridge 182. Then, a first end of a surgical suture "S3" is inserted into one of the pair of distal recesses 182f and a second end of surgical suture "S3" is extended across the surgical cartridge buttress and inserted into the other of the pair of distal recesses 182f. It is contemplated that at least the recess 182f that is adjacent the retainer 195 is an open ended constricting slot so as to frictionally grip or cinch a surgical suture "S3" disposed therein.

In operation, with surgical cartridge buttress (not shown) secured against the tissue contacting surface of staple cartridge 182, during firing of surgical stapling apparatus 10, as drive assembly 150 is advanced (i.e., moved from a proximal-most position to a distal-most position), knife blade 166 slices through a central section of a proximal suture (not shown), thereby freeing the proximal end of the surgical cartridge buttress from staple cartridge 182. During use, as the firing stroke of surgical stapling apparatus 10 is nearing completion and as drive assembly 150 approaches a distal end of central longitudinal slot 182c of staple cartridge 182, as seen in FIG. 25, drive assembly 150 contacts living hinge connection 196d between first leg member 196b and second leg member 196c. As drive assembly 150 is further advanced distally, drive assembly 150 presses against living hinge connection 196d, causing first leg member 196b and second leg member 196c to extend. As first leg member 196b and second leg member 196c extend, piston 196e is translated through recess 195c of retainer 195. As piston 196e is translated through recess 195c of retainer 195, piston 196e engages the second end of suture "S3" and urges suture "S3" out of the distal recess 182f that is registration therewith to release the second end of suture "S3" therefrom. With the second end of surgical suture "S3" released or free from distal recess 182f, the distal end of the surgical cartridge buttress "B" is free to separate from the tissue contacting surface of staple cartridge 182.

Turning now to FIGS. 26-29, a loading unit according to another embodiment of the present disclosure, for surgical stapling apparatus 10, is generally designated as 216. Loading unit 216 is substantially similar to loading unit 16 or 116 and will only be discussed in detail herein to the extent necessary to identify differences in construction and operation.

As seen in FIGS. 26-29, anvil assembly 220 of loading unit 216 includes a release assembly 274 disposed between anvil plate 270 and cover plate 272 at a location in operative registration with the distal pair of recesses 270e. Release assembly 274 includes a cam 275 pivotally connected to anvil plate 270 and/or cover plate 272. Cam 275 includes a body portion 275a having an ovular profile and defining a cam surface 275b that is in operative association with one of the distal pair of recesses 270e. Cam 275 further includes a finger or stem 275c projecting at an angle from a lateral edge of body portion 275a.

Figure 27:
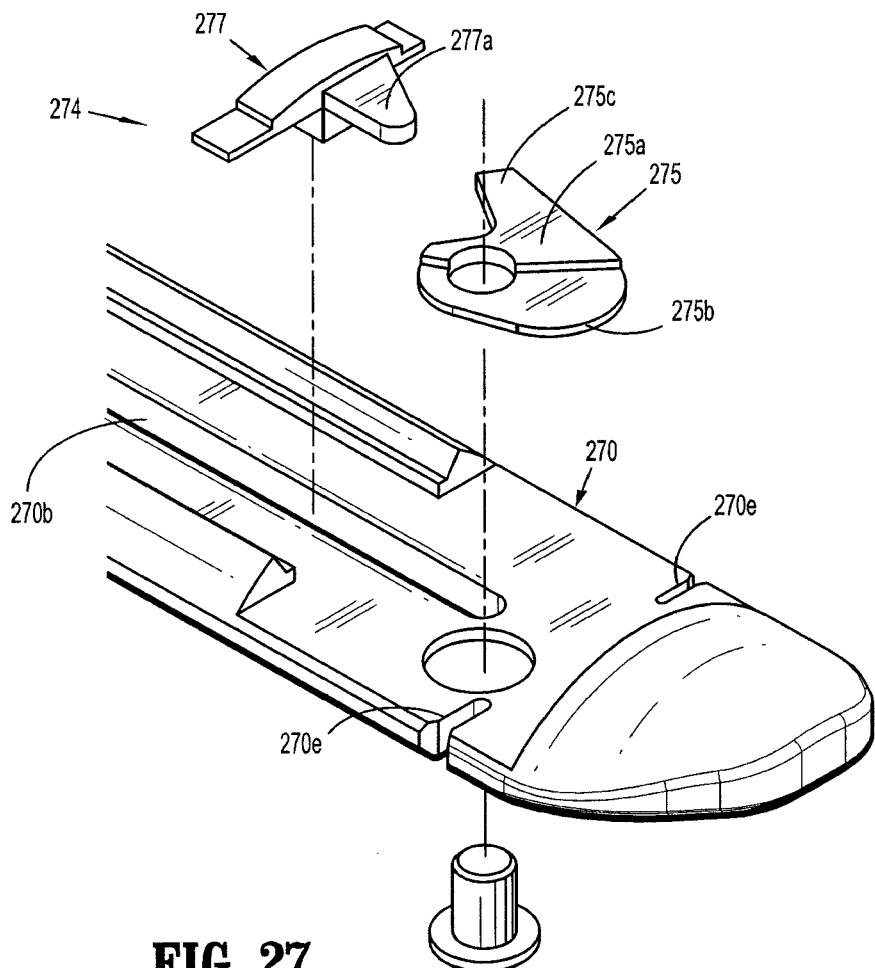
FIG. 27 is a top, perspective view, with parts separated, of the distal end of the anvil assembly of FIG. 26.
Figure 28:
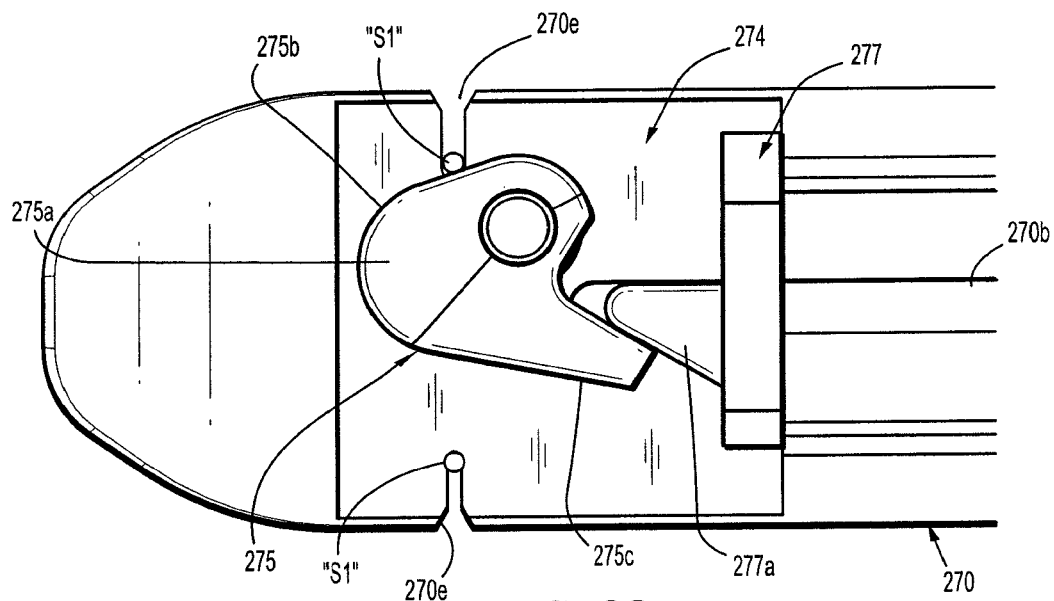
FIG. 28 is a top, plan view of the distal end of the anvil assembly of FIGS. 26 and 27, illustrating the suture release assembly thereof in an unactuated configuration.
Figure 29:
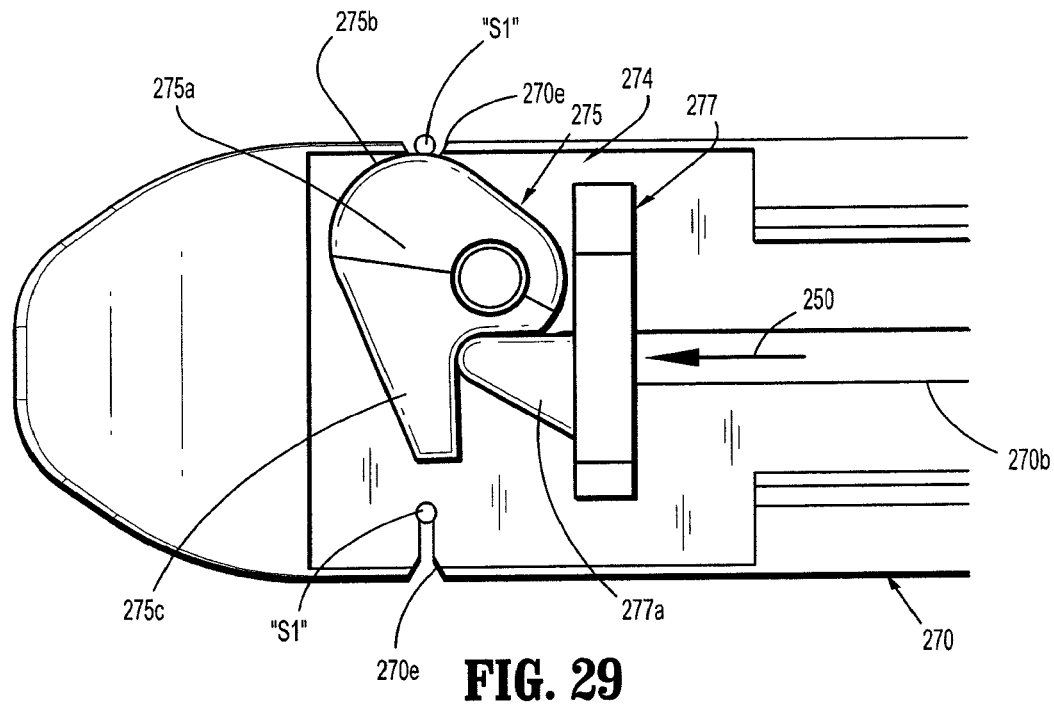
FIG. 29 is a top, plan view of the distal end of the anvil assembly of FIGS. 26-28, illustrating the suture release assembly thereof in an actuated configuration.

Release assembly 274 further includes a pusher 277 slidably disposed between anvil plate 270 and cover plate 272. As seen in FIGS. 27-29, pusher 277 may be slidably disposed within longitudinal slot 270b of anvil plate 270a. Pusher 277 includes a cam arm 277a extending substantially in a distal direction. Cam arm 277a is configured and dimensioned to engage and/or act on finger 275c extending from cam 275.

As seen in FIG. 28, suture release assembly 274 includes an unactuated configuration wherein body portion 275a of cam 275 does not extend into or overlie the respective one of the pair of distal recesses 270e in operative registration therewith, and pusher 277 is in a retracted or non-advanced position. As seen in FIG. 28, cam arm 277a of pusher 277 is adjacent finger 275c and may, although not necessarily, be in contact with finger 275c of cam 275.

As seen in FIG. 29, suture release assembly 274 includes an actuated configuration wherein body portion 275a of cam 275 extends into or overlies the respective one of the pair of distal recesses 270e in operative registration therewith, and pusher 277 is in an advanced position. As seen in FIG. 29, when pusher 277 is in the advanced position, cam arm 277a of pusher 277 has engaged finger 275c of cam 275 to rotate body portion 275a of cam 275.

In operation, with an surgical anvil buttress (not shown) secured against the lower surface of anvil plate 270, during firing of the surgical stapling apparatus, as drive assembly 250 approaches a distal-most end of knife slot 270b of anvil plate 270, drive assembly 250 contacts pusher 277, thus driving pusher 277 distally. As pusher 277 is driven distally, as seen in FIGS. 28 and 29, cam arm 277a of pusher 277 engages finger 275c of cam 275 to rotate or pivot cam 275. As cam 275 is rotated, cam surface 275b of cam 275 comes into contact with and urges the second end of suture "S1" out of the distal recess 270e that is registration therewith to release the second end of suture "S1" therefrom. With the second end of surgical suture "S1" released or free from distal recess 270e, the distal end of the surgical anvil buttress is free to separate from the tissue contacting surface of anvil plate 270.

Figure 30:
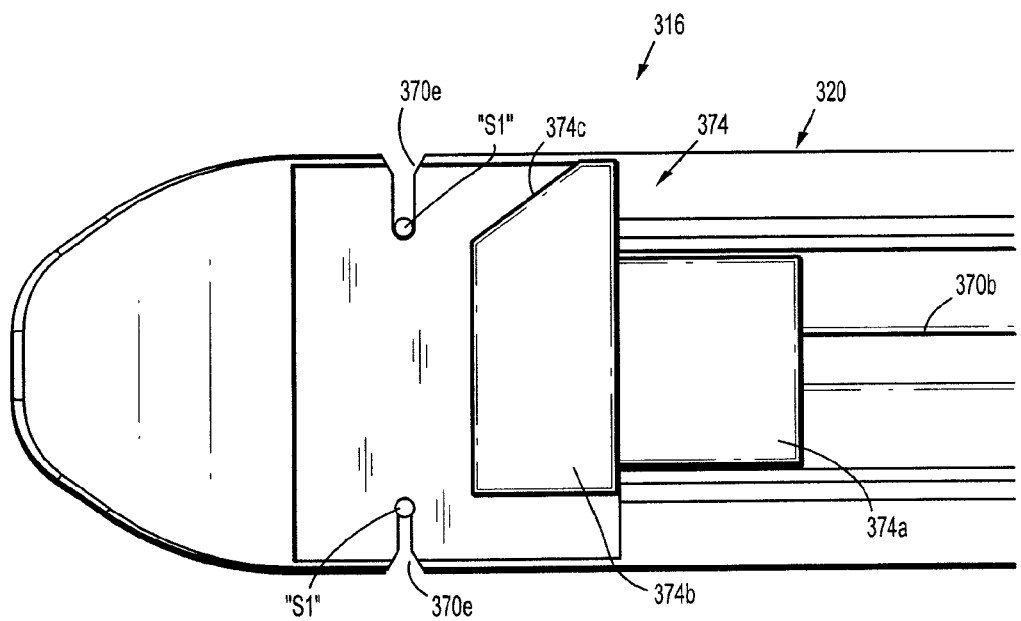
FIG. 30 is a top, plan view of a distal end of an anvil assembly of a loading unit including a suture release assembly according to still another embodiment of the present disclosure, illustrating the suture release assembly thereof in an unactuated configuration.
Figure 31:
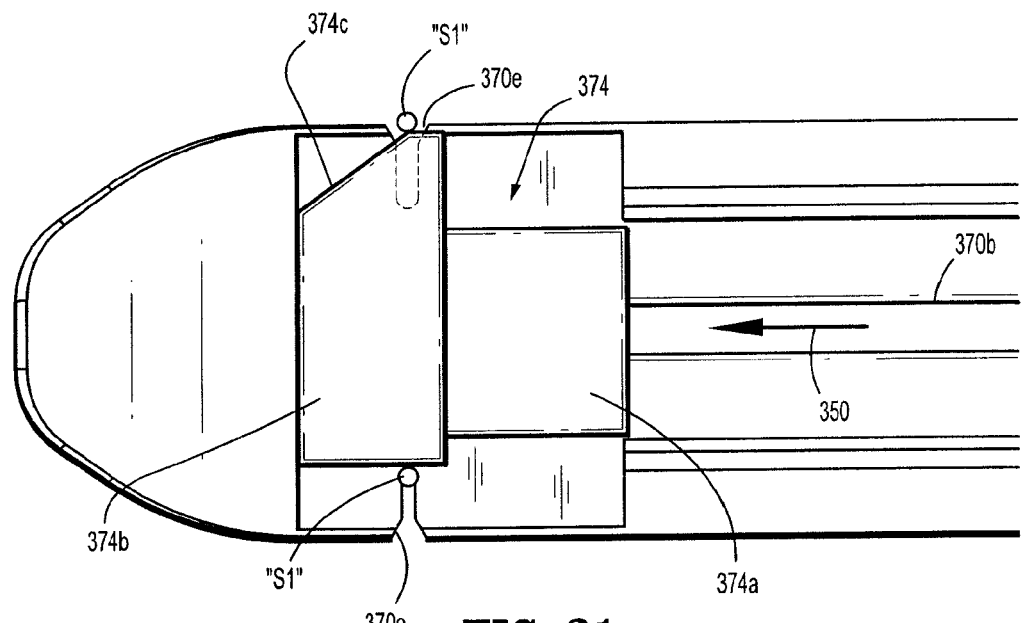
FIG. 31 is a top, plan view of the distal end of the anvil assembly of FIG. 30, illustrating the suture release assembly thereof in an actuated configuration.
Figure 32:
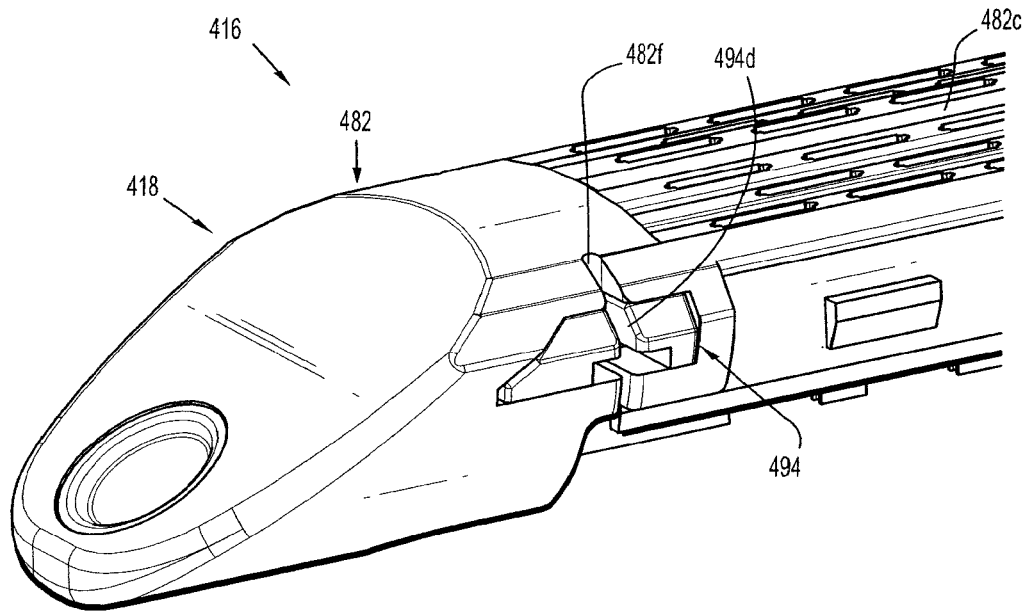
FIG. 32 is a top, perspective view of a distal end of a cartridge assembly of a loading unit including a suture release assembly according to a further embodiment of the present disclosure.
Figure 33:
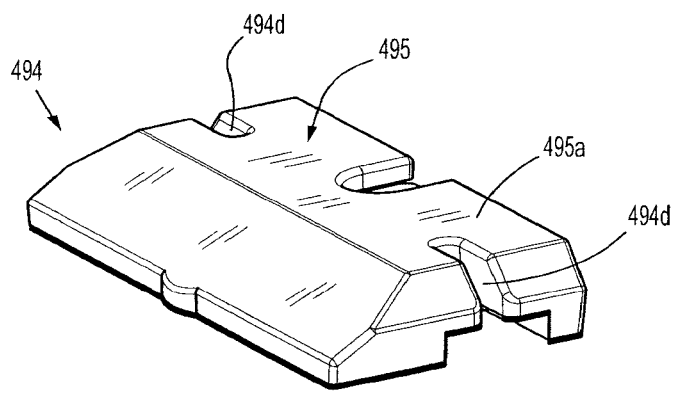
FIG. 33 is a top, perspective view of the suture release assembly of FIG. 32.
Figure 34:
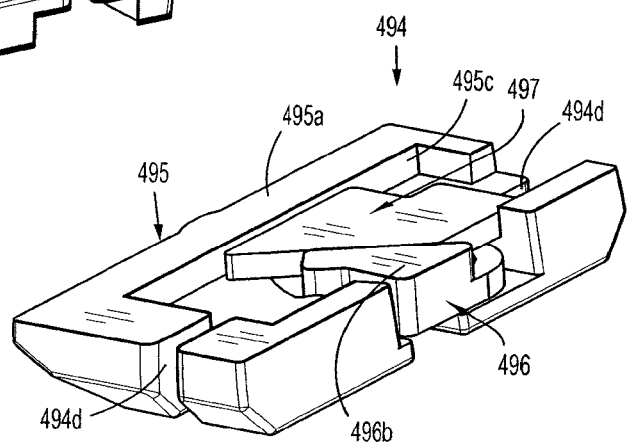
FIG. 34 is a bottom, perspective view of the suture release assembly of FIGS. 32 and 33.

Turning now to FIGS. 30 and 31, a loading unit according to another embodiment of the present disclosure, for surgical stapling apparatus 10, is generally designated as 316. Loading unit 316 is substantially similar to loading unit 16, 116 or 216 and will only be discussed in detail herein to the extent necessary to identify differences in construction and operation.

As seen in FIGS. 30 and 31, anvil assembly 320 of loading unit 316 includes a release assembly 374 disposed between anvil plate 370 and the cover plate at a location in operative registration with the distal pair of recesses 370e. Release assembly 374 includes a body portion 374a slidably disposed within longitudinal slot 370b of anvil plate 370a. Release assembly 374 further includes a head portion 374b connected to or extending from a distal surface of body portion 374a. Head portion 374b defines a cam surface 374c along a side edge thereof that is configured and dimensioned for operatively association with one of the distal pair of recesses 370e formed in anvil plate 370a. Cam surface 374c may have an arcuate, curved or sinusoidal profile.

As seen in FIG. 30, suture release assembly 374 includes an unactuated configuration wherein body portion 374a is retracted and cam surface 374c does not extend into or across the respective one of the pair of distal recesses 370e in operative registration therewith.

As seen in FIG. 31, suture release assembly 374 includes an actuated configuration wherein body portion 374a is advanced distally and cam surface 374c extends into or overlies the respective one of the pair of distal recesses 370e in operative registration therewith.

In operation, with a surgical anvil buttress (not shown) secured against the lower surface of anvil plate 370, during firing of the surgical stapling apparatus, as drive assembly 350 approaches a distal-most end of knife slot 370b of anvil plate 370, as seen in FIGS. 30 and 31, drive assembly 350 contacts body portion 374a of release assembly 374, thus driving head portion 374b distally. As head portion 374b is driven distally, cam surface 374c comes into contact with and urges the second end of suture "S1" out of the distal recess 370e that is registration therewith to release the second end of suture "S10" released or free from distal recess 370e, the distal end of the surgical anvil buttress is free to separate from the tissue contacting surface of anvil plate 370.

In a further embodiment, the driving head portion may include a sharpened edge instead of cam surface 374c. As the driving head portion is moved distally, the suture "S1" is caught between the sharpened edge of the driving head portion and the side of the distal recess 370e, severing the suture "S1."

Turning now to FIGS. 32-38, a loading unit according to another embodiment of the present disclosure, for surgical stapling apparatus 10, is generally designated as 416. Loading unit 416 is substantially similar to loading unit 16, 116, 216 or 316 and will only be discussed in detail herein to the extent necessary to identify differences in construction and operation.

As seen in FIGS. 32-38, cartridge assembly 418 of loading unit 416 includes a cartridge release assembly 494 supported in and near a distal end of staple cartridge 482. Release assembly 494 includes a retainer 495 supported in a distal end of staple cartridge 482 at a location near a distal end of longitudinal slot 482c and at least partially extending thereacross. Retainer 495 includes a body portion 495a, a boss 495b extending from a surface thereof, and defines a channel or recess 495c formed in a surface thereof and extending through a side thereof. Body portion 495a of retainer 495 defines a slot 495d formed in opposed sides thereof and which are configured to receive a suture therein. When supported in staple cartridge 482, recess 495c of retainer 495 is in registration with one of the pair of distal recesses 482f of staple cartridge 482, and slots 495d of retainer 495 are in registration with the pair of distal recesses 482f of staple cartridge 482 (see FIG. 32).

Release assembly 494 further includes a cam member 496 having a head portion 496a pivotally connected to boss 495b of retainer 495. Cam member 496 further includes a body portion 496b extending from head portion 496a. Body portion 496b defines a first cam surface 496c and a second cam surface 496d each extending substantially tangentially to an axis of rotation of cam member 496.

Release assembly 494 further includes a sled 497 slidably disposed within channel 495c of retainer 495. Sled 497 includes a body portion 497a defining a cam surface 497b oriented to operatively engage second cam surface 496d of cam member 496, and a side wall 497c in registration with the one of the pair of distal recesses 482f of staple cartridge 482 that is in registration with recess 495c of retainer 495.

As seen in FIG. 37, release assembly 494 includes an unactuated configuration wherein first cam surface 496c of cam member 496 extends across longitudinal slot 482c staple cartridge 482, side wall 497c of sled 497 does not extend into or over the one of the pair of distal recesses 482f of staple cartridge 482 that is in registration therewith, and second cam surface 496d of cam member 496 is substantially in flush contact with cam surface 497b of sled 497.

As seen in FIG. 38, release assembly 494 includes an actuated configuration wherein first cam surface 496c of cam member 496 does not substantially extend across longitudinal slot 482c of staple cartridge 482, side wall 497c of sled 497 extends into or over the one of the pair of distal recesses 482f of staple cartridge 482 that is in registration therewith, and second cam surface 496d of cam member 496 is spaced away from cam surface 497b of sled 497.

With reference to FIGS. 32-38, during the manufacturing process, with suture release assembly 494 in the unactuated configuration, a surgical cartridge buttress (not shown) is laid over the tissue contacting surface of staple cartridge 482. Then, a first end of a surgical suture "S3" is inserted into one of the pair of distal recesses 482f and a second end of surgical suture "S3" is extended across the surgical cartridge buttress and inserted into the other of the pair of distal recesses 482f. It is contemplated that at least the distal recesses 482f adjacent the side wall 497c is an open ended constricting slot so as to frictionally grip or cinch a surgical suture "S3" disposed therein.

In operation, with a surgical cartridge buttress (not shown) secured against the tissue contacting surface of staple cartridge 482, during firing of the surgical stapling apparatus, as drive assembly 450 approaches a distal end of central longitudinal slot 482c of staple cartridge 482, as seen in FIG. 38, drive assembly 450 contacts second cam surface 496c of cam member 496 extending across longitudinal slot 482c of staple cartridge 482.

As drive assembly 450 is further advanced distally, drive assembly 450 presses against first cam surface 496c of cam member 496, causing cam member 496 to rotate. As cam member 496 is rotated, second cam surface 496d thereof contacts and presses against cam surface 497b of sled 497 thus causing sled 497 to translate in recess 495c of retainer 495. As sled 497 is translated through recess 495c, side wall 497c of sled 497 engages the second end of suture "S3" and urges suture "S3" out of the distal recess 482f that is registration therewith to release the second end of suture "S3" therefrom. With the second end of surgical suture "S3" released or free from distal recess 482f, the distal end of the surgical cartridge buttress is free to separate from the tissue contacting surface of staple cartridge 482.

According to further embodiments of the present disclosure, it is contemplated that buttresses "B" may be provided or formed with integral wings or tabs extending therefrom for insertion and/or receipt into distal and/or proximal recesses of anvil assembly and/or cartridge assembly. It is further contemplated that sutures "S" may be affixed to, embedded in or other wise connected to buttresses "B."

Exemplary surgical buttresses "B" for use with the surgical stapling devices disclosed herein are shown and described in commonly assigned U.S. Pat. Nos. 5,542,594; 5,908,427; 5,964,774; 6,045,560; 7,823,592; and 7,938,307, the entire contents of each of which is incorporated herein by reference.

Surgical buttresses "B" may be fabricated from a suitable biocompatible and bioabsorbable material. Surgical buttresses "B" may be fabricated from a non-absorbent material which does not retain fluid. Surgical buttresses "B" may be fabricated from "BIOSYN" made from GLYCOMER 631 (a block copolymer), a synthetic polyester composed of glycolide, dioxanone and trimethylene carbonate.

One block of the resulting copolymer contains randomly combined units derived from p-dioxanone (1,4-dioxan-2-one) and trimethylene carbonate (1,3-dioxan-2-one). The second block of the copolymer contains randomly combined units derived from glycolide and p-dioxanone. The resulting polyester is an ABA triblock terpolymer possessing about 60% glycolide, about 14% dioxanone, and about 26% trimethylene carbonate.

It will be understood that various modifications may be made to the embodiments disclosed herein. For example, the stapling apparatus need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodiments. Those skilled in the art will envision other modifications within the scope and spirit of the claims appended thereto.

What is claimed is:

1. A method of attaching a surgical buttress to a surgical instrument, comprising:
   providing a surgical instrument including a cartridge assembly and an anvil assembly;
   providing at least one surgical buttress;
   providing at least one connecting member;
   extending the connecting member across the at least one surgical buttress; and
   securing the at least one connecting member to a constricting slot of one of the cartridge assembly and the anvil assembly.

2. The method of claim 1, further comprising lying the at least one surgical buttress across a tissue contacting surface of one of the cartridge assembly and the anvil assembly.

3. The method of claim 1, wherein the constricting slot has a converging shape.

4. The method of claim 1, wherein at least one of the cartridge assembly and the anvil assembly has a pair of constricting slots, and the at least one connecting member has a first and a second end.

5. The method of claim 4, wherein the first end is secured to a first of the pair of constricting slots and the second end is secured to a second of the pair of constricting slots.

6. The method of claim 5, wherein the first of the pair of constricting slots is wider than the second of the pair of constricting slots.

7. The method of claim 6, wherein the second end is secured before the first end.

8. The method of claim 1, wherein the surgical instrument includes a release assembly.

9. The method of claim 1, wherein the at least one surgical buttress includes a surgical buttress for the cartridge assembly and a surgical buttress for the anvil assembly.

10. The method of claim 9, further comprising securing the at least one connecting member to the constricting slot of the anvil assembly.

11. A method of attaching a surgical buttress to a surgical apparatus, comprising:
    providing a surgical apparatus including a cartridge assembly and an anvil assembly;
    providing at least one surgical buttress;
    providing at least one fastener;
    extending the fastener across the at least one surgical buttress; and
    securing the at least one connecting member to a constricting slot of one of the cartridge assembly and the anvil assembly.

12. The method of claim 11, further comprising lying the at least one surgical buttress across a tissue contacting surface of one of the cartridge assembly and the anvil assembly.

13. The method of claim 11, wherein the constricting slot has a converging shape.

14. The method of claim 11, wherein at least one of the cartridge assembly and the anvil assembly has a pair of constricting slots, and the at least one fastener has a first and a second end.

15. The method of claim 14, wherein the first end is secured to a first of the pair of constricting slots and the second end is secured to a second of the pair of constricting slots.

16. The method of claim 15, wherein the first of the pair of constricting slots is wider than the second of the pair of constricting slots.

17. The method of claim 16, wherein the second end is secured before the first end.

18. The method of claim 11, wherein the surgical apparatus includes a release assembly.

19. The method of claim 11, wherein the at least one surgical buttress includes a surgical buttress for the cartridge assembly and a surgical buttress for the anvil assembly.

20. The method of claim 19, further comprising securing the at least one fastener to the constricting slot of the anvil assembly.

* * * * *